(12) United States Patent
Treneman et al.

(10) Patent No.: US 11,964,097 B2
(45) Date of Patent: Apr. 23, 2024

(54) INHALER

(71) Applicant: ASTRAZENECA AB, Sodertalje (SE)

(72) Inventors: Bill Treneman, Suffolk (GB);
Charlotte Leeder, Suffolk (GB);
Andrew Halket, Suffolk (GB); Simon Ingram, Cambridge (GB); Chris Hurlstone, Cambridge (GB); Valerio Lelio Cereda, Cambridge (GB); Joe Daintrey, Cambridge (GB); Warren Isaacs, Cambridge (GB); Martin Karlsson, Cambridge (SE); Jake Christofferson, Sodertalje (SE); Rune Ducce, Soldertalje (SE); Simon Berry, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 766 days.

(21) Appl. No.: 16/978,250

(22) PCT Filed: Mar. 6, 2019

(86) PCT No.: PCT/EP2019/055521
§ 371 (c)(1),
(2) Date: Sep. 4, 2020

(87) PCT Pub. No.: WO2019/170718
PCT Pub. Date: Sep. 12, 2019

(65) Prior Publication Data
US 2021/0008302 A1    Jan. 14, 2021

Related U.S. Application Data

(60) Provisional application No. 62/639,704, filed on Mar. 7, 2018.

(51) Int. Cl.
*A61M 15/00*    (2006.01)

(52) U.S. Cl.
CPC ...... *A61M 15/002* (2014.02); *A61M 15/0013* (2014.02); *A61M 15/0025* (2014.02);
(Continued)

(58) Field of Classification Search
CPC .......... A61M 15/0025; A61M 15/0026; A61M 15/002; A61M 15/0013; A61M 15/0086;
(Continued)

(56) References Cited

U.S. PATENT DOCUMENTS 3,456,644 A * 7/1969 Thiel ................ A61M 15/0091
128/200.23
3,598,294 A * 8/1971 Hedrick ............ A61M 15/0096
222/402.2

(Continued)

FOREIGN PATENT DOCUMENTS

GB          2461153 A * 12/2009 ........ A61M 15/0091
WO    2000/016837 A1    3/2000
(Continued)

*Primary Examiner* — Tu A Vo

(57) ABSTRACT

An inhaler for delivery of a medicament by inhalation includes an inhaler body for receiving a canister having a dispensing valve. A drive mechanism is provided for driving the canister from a rest position in which the valve is closed to an actuating position in which the valve is open. A resetting mechanism is provided for resetting the drive mechanism. A return mechanism is provided for returning the canister from the actuating position to the rest position, wherein the return mechanism comprises a damping system that is configured to enable the canister to automatically return from the actuating position to the rest position within a predetermined time period. A method of operation of an inhaler is also disclosed.

18 Claims, 30 Drawing Sheets

(52) U.S. Cl.
CPC .... *A61M 15/0026* (2014.02); *A61M 15/0086* (2013.01); *A61M 15/009* (2013.01); *A61M 15/0091* (2013.01); *A61M 15/0095* (2014.02); *A61M 15/0071* (2014.02); *A61M 15/0096* (2014.02); *A61M 2205/8281* (2013.01)

(58) Field of Classification Search
CPC ...... A61M 15/0091; A61M 2205/8281; A61M 15/0095; A61M 15/0093; A61M 15/0096; A61M 15/009
See application file for complete search history.

(56) References Cited

U.S. PATENT DOCUMENTS

| | | | | |
|---|---|---|---|---|
| 4,803,978 A | * | 2/1989 | Johnson, IV | A61M 15/0091 128/204.26 |
| 5,347,998 A | * | 9/1994 | Hodson | A61M 15/0095 128/200.23 |
| 6,672,304 B1 | | 1/2004 | Casper | |
| 2002/0088458 A1 | * | 7/2002 | Christrup | A61M 15/0068 128/200.14 |
| 2004/0237961 A1 | * | 12/2004 | Snow | A61M 15/0068 128/200.23 |
| 2005/0066961 A1 | * | 3/2005 | Rand | A61M 15/0068 128/200.14 |
| 2006/0243275 A1 | * | 11/2006 | Ruckdeschel | A61M 15/0091 128/200.23 |
| 2008/0178872 A1 | * | 7/2008 | Genova | A61M 15/0065 128/200.23 |
| 2019/0022339 A1 | * | 1/2019 | Richardson | A61M 15/009 |
| 2019/0111220 A1 | * | 4/2019 | Richardson | A61M 15/009 |
| 2019/0351160 A1 | * | 11/2019 | Stuart | A61M 15/0091 |

FOREIGN PATENT DOCUMENTS

| | | |
|---|---|---|
| WO | 2013/038169 A1 | 3/2013 |
| WO | 2013/038170 A2 | 3/2013 |

* cited by examiner

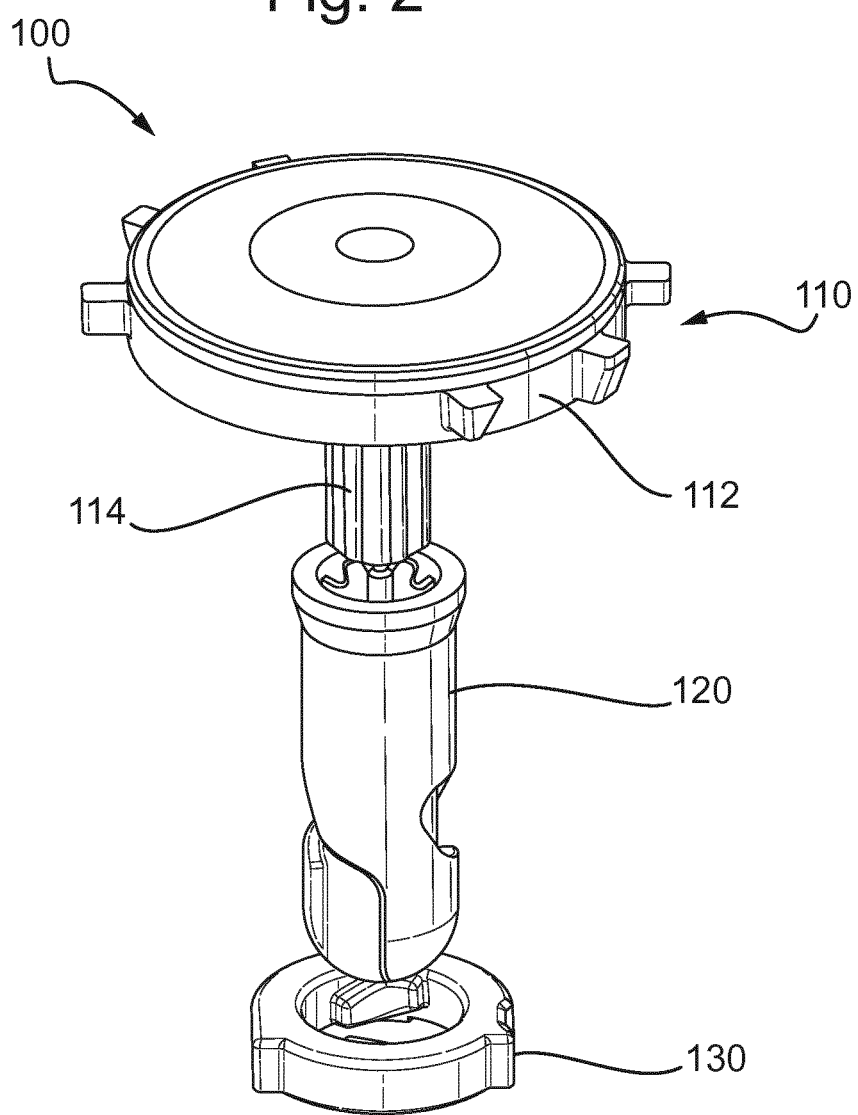

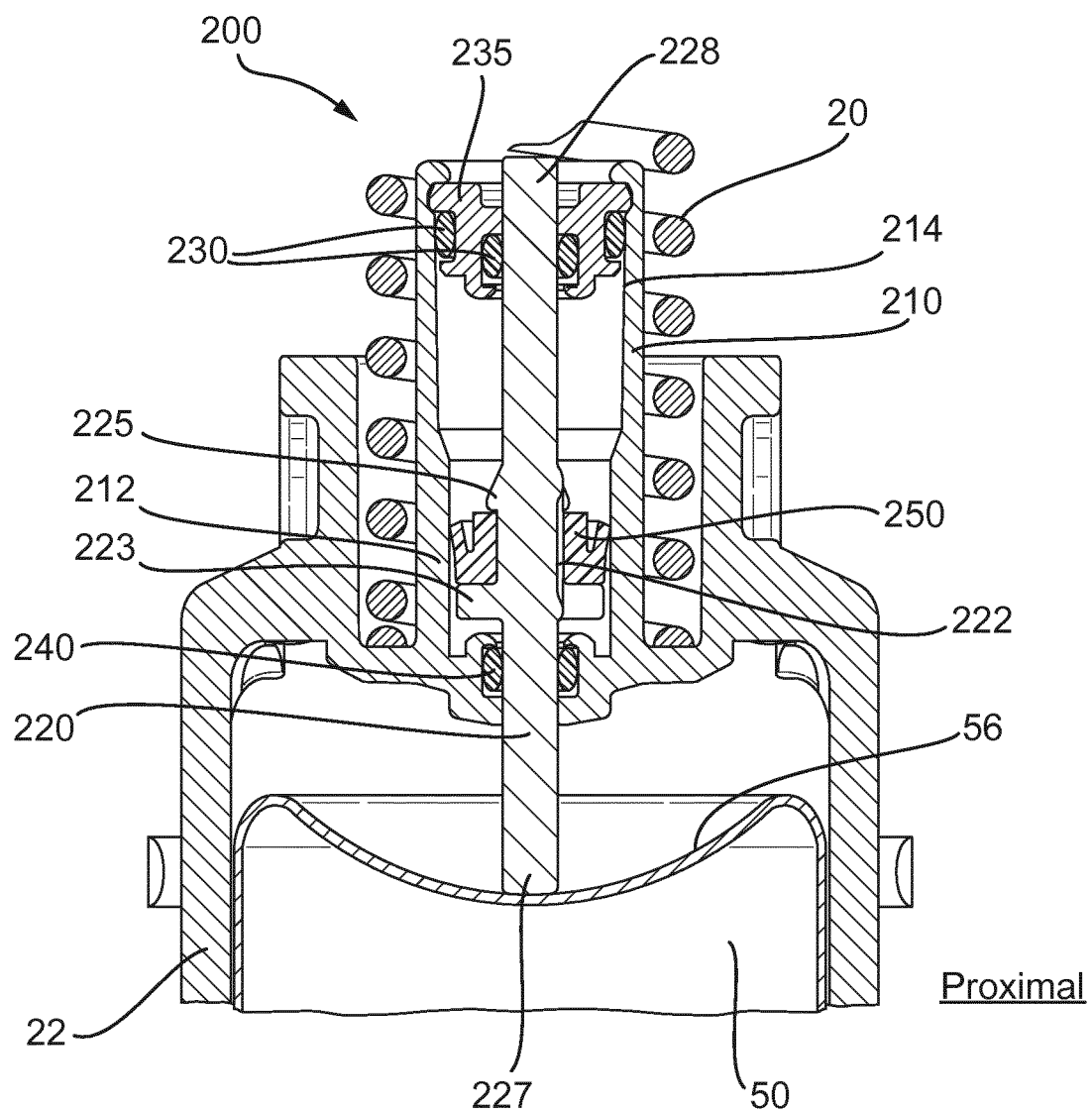

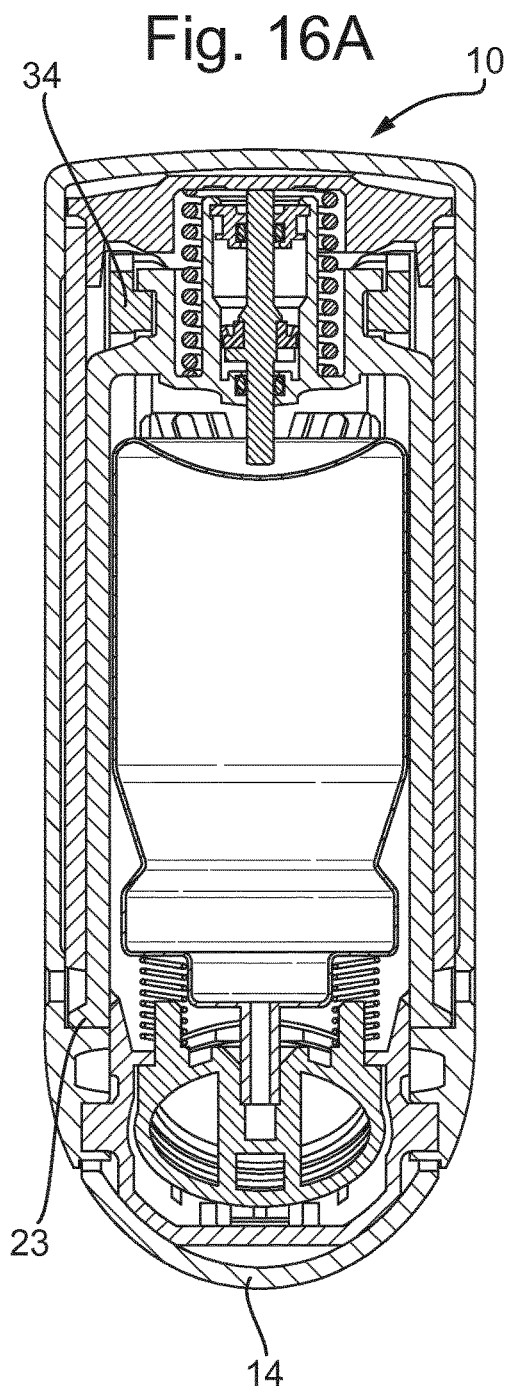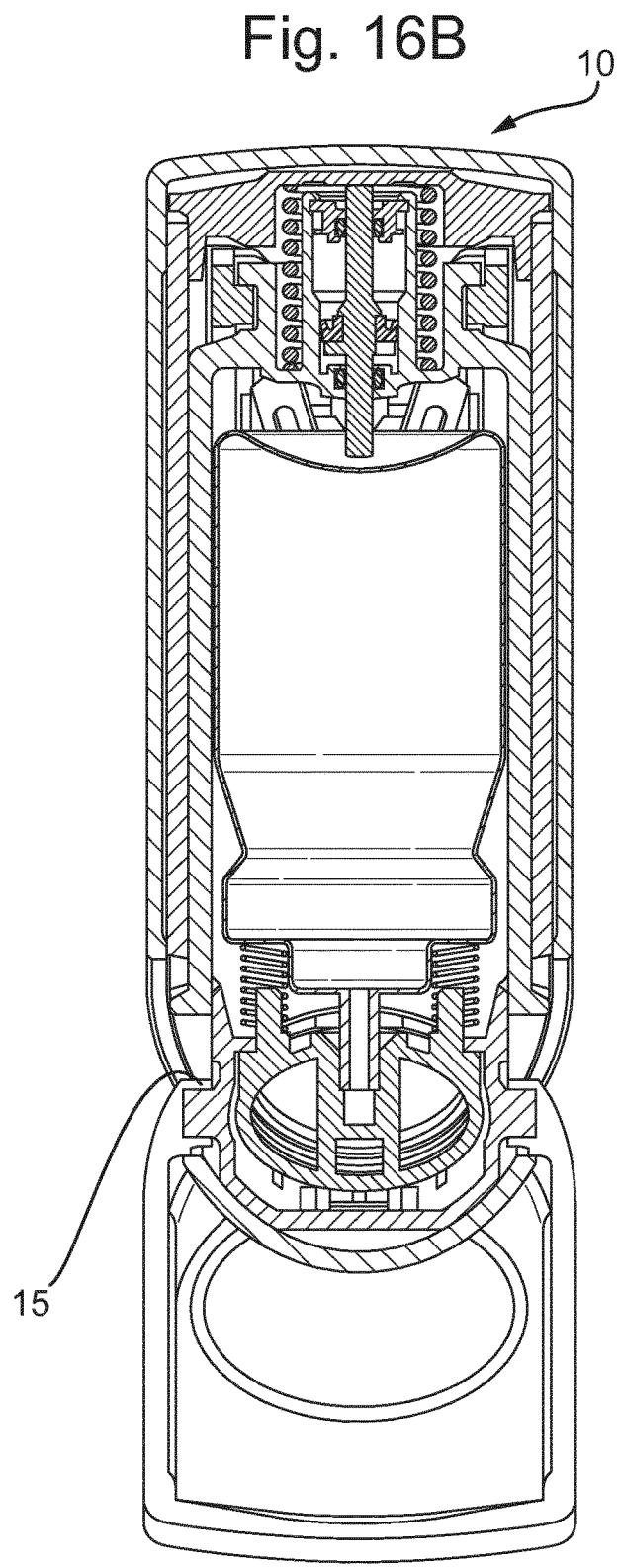

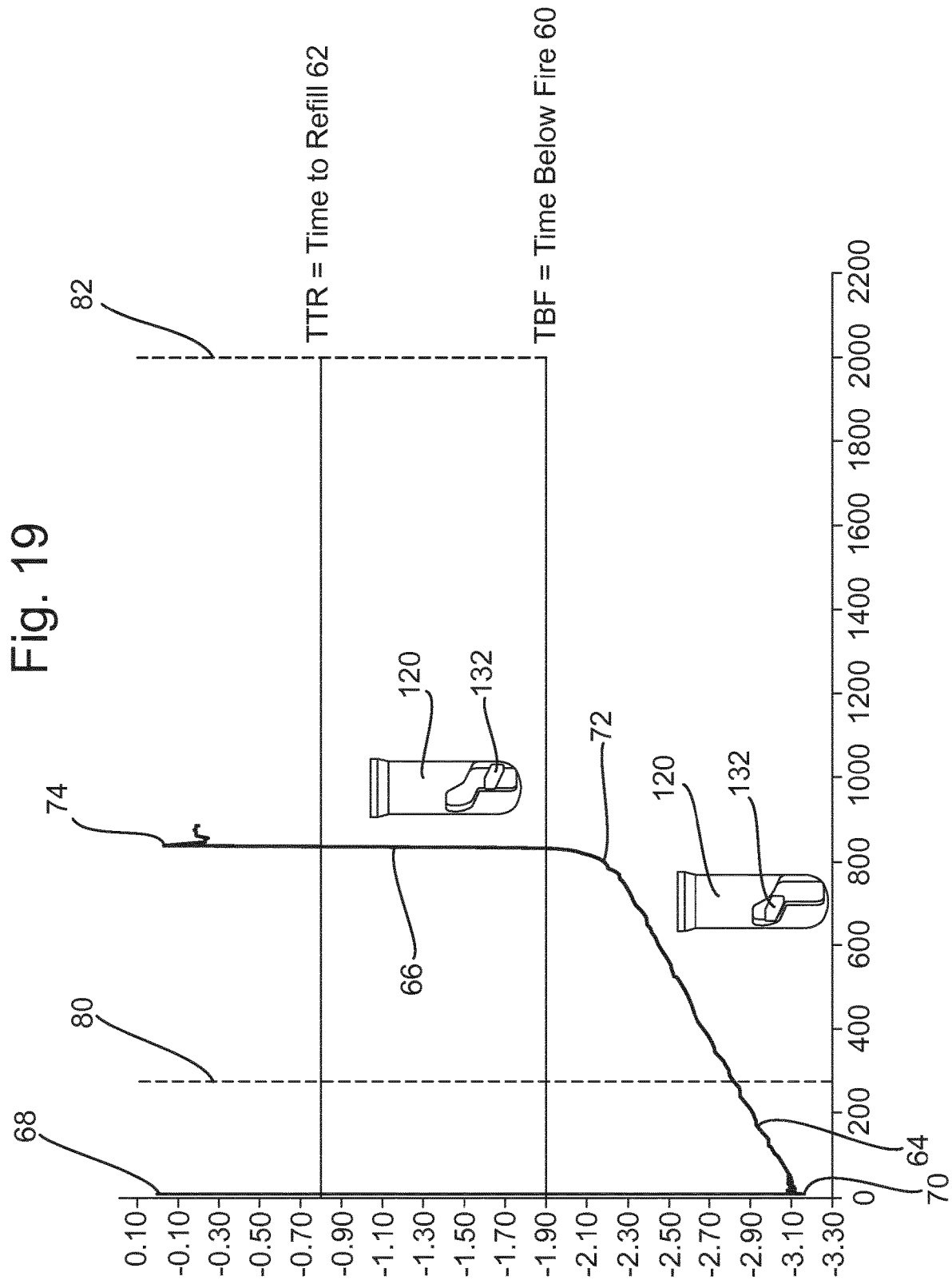

INHALER

CROSS-REFERENCE TO RELATED APPLICATIONS

This application is a U.S. National Stage application of International Application No. PCT/EP2019/055521, filed on Mar. 6, 2019, said International Application No. PCT/EP2019/055521 claims benefit under 35 U.S.C. § 119(e) of the U.S. Provisional Application No. 62/639,704, filed Mar. 7, 2018. Each of the above listed applications is incorporated by reference herein in its entirety for all purposes.

TECHNICAL FIELD

The present invention relates to an inhaler for delivery of a medicament by inhalation and methods of operation thereof, and in particular to the mechanisms of the inhaler for dispensing a dose of medicament and to the resetting of the mechanisms for dispensing a subsequent dose. The present invention also relates to a method of dispensing medicament from an inhaler, and in particular to a method of dispensing a dose of medicament from the inhaler and resetting the inhaler for dispensing a subsequent dose.

BACKGROUND OF THE INVENTION

There are many ways to provide a dose of medicament to a patient or other intended recipient of the medicament, particularly when it is desired to provide multiple doses of the medicament, for example as part of a treatment regimen or otherwise. Many medicaments, such as those for treating pulmonary or other conditions, are delivered/dispensed to the recipient by inhalation using a suitable inhaler. One commonly used and effective type of multiple dose inhaler is a pressurised metered dose inhaler (pMDI) in which a canister containing medicament in the inhaler is actuated, e.g. by compression, to deliver/dispense a metered dose of the medicament through a mouthpiece to a user. The inhaler may be configured to deliver/dispense a dose of medicament automatically. For example the inhaler may comprise an actuation mechanism to actuate the canister when triggered. The actuation mechanism may be breath-actuated, i.e. triggered by inhalation of a user through a mouthpiece. This ensures that a dose of medicament is dispensed whilst the user is inhaling, which is particularly advantageous since dispensing of a dose of medicament is co-ordinated with inhalation of the dose and synchronisation of the patient's breath-intake (or inspiration) ensures optimal delivery of aerosol medication to the target region in the respiratory tract, with minimal losses due to deposition in the mouth and pharynx. For multiple dose inhalers, the triggering and dispensing mechanisms must be reset after each actuation to enable a subsequent dose to be dispensed when required.

An example breath-actuated pMDI is described in WO-A-2013/038170. The actuation mechanism of this inhaler is operable to compress a canister containing medicament to deliver a metered dose of the medicament in response to inhalation by a user. The actuation mechanism comprises a spring to compress the canister and a trigger mechanism to prevent the spring compressing the canister until a dose is to be dispensed. When a user inhales through a mouthpiece, the trigger mechanism releases the spring, which then compresses the canister to deliver a dose of medicament through a valve of the canister and into the mouthpiece. A resetting mechanism interacts with a cover or cap for the mouthpiece such that movement of the cover into a closed position resets the spring.

Whilst the inhaler disclosed in this application is effective and reliable at dispensing multiple, consecutive doses to a user, it has been observed that in some circumstances, the consecutive doses dispensed from the inhaler may not have a consistent weight of active ingredient (known as actuation weight). Without intending to be bound by any theory, it is believed that this inconsistency in actuation weight (and thus variation in the delivered dose) may occur from user error, because the user of the inhaler does not reset the dispensing mechanism immediately after dispensing a dose (i.e. does not close the mouthpiece cover straight away). Additionally or alternatively, the canister should be reset with the valve in position beneath the canister, but the user may not always follow this instruction. Either of these problems may lead to the metering chamber of the canister valve being incompletely filed and thus the next dose dispensed from the canister valve may not contain the expected weight of medicament.

Therefore there remains a need for an inhaler for delivery of a medicament by inhalation, and a method of dispensing a medicament from an inhaler, in which the delivered dose upon each actuation is consistent and within acceptable tolerances, compared with other doses dispensed by the inhaler.

SUMMARY OF THE INVENTION

In accordance with the present invention, there is provided an inhaler for delivery of a medicament by inhalation and a method of dispensing a medicament from an inhaler, which overcome at least one or more of the drawbacks of the prior art. From a first broad aspect, there is provided an inhaler for delivery of a medicament by inhalation, the inhaler comprising an inhaler body for receiving a canister having a dispensing valve; a drive mechanism comprising a biasing means and a moving component, the drive mechanism for driving the canister, when received in the inhaler body, from a rest position in which the valve is closed to at least an actuating position in which the valve is open, the drive mechanism driving the canister when the biasing means is released from a loaded configuration to move the moving component from a first position to a second position; a resetting mechanism for resetting the drive mechanism by moving the moving component from the second position to the first position and reloading the biasing means to the loaded configuration; and a return mechanism for returning the canister from the actuating position to the rest position; wherein the return mechanism comprises a damping system, the damping system configured to enable the canister to automatically return from the actuating position to the rest position within a predetermined time period measured from the release of the biasing means from the loaded configuration.

The claimed inhaler overcomes at least one of the drawbacks of the prior art. For example, the inhaler automatically returns the canister from the actuating position to the rest position, within a predetermined time period, such that the canister valve is returned to its refill point and refilled for a subsequent dose all within this time, irrespective of whether the user of the inhaler activates the resetting mechanism to restore the inhaler to its pre-fire configuration. This occurs over a period of time sufficient for the valve to dispense the entire current dose as the damping mechanism is configured to prevent the canister return occurring too quickly. Namely the valve is held open for a sufficient time to dispense the dose and the valve is returned at a suitable speed to allow the valve to refill completely, but the valve is not held in an open configuration for any longer than is necessary to perform these actions reliably. Furthermore, the valve is reset to its closed position sufficiently quickly that the user will still be holding the inhaler in an upright position, so the valve will be located beneath the canister.

Whilst the canister reset could be performed as a single step at one speed for the entire time period, optionally the damping system is configured such that the predetermined time period comprises a first time segment and a second time segment, wherein movement of the canister from the actuating position to the rest position is slower during the first time segment than during the second time segment. This arrangement optimises the time during which the valve is held open below its fire point (hereinafter referred to as Time Below Fire (TBF)) and so dispenses the entire dose effectively, but also minimises the time before the canister valve reaches its refill point (hereinafter referred to as Time To Refill (TTR)). As discussed above, all this occurs without the user needing to take any action as it is automatic and controlled by the damping mechanism. In some embodiments, during the first time segment the canister is maintained in the actuating position (i.e. there is no movement) and during the second time segment the canister returns from the actuating position to the rest position.

Whilst the predetermined time period might include other time segments, optionally the damping system is configured such that the second time segment immediately follows the first time segment, so the canister movement transitions immediately from slow return or substantially no movement to fast or faster return without any pause or delay inbetween.

Canisters for use in inhalers according to embodiments of the present invention have generally consistent profiles and configurations but differences between canisters due to tolerances should be expected and also the same canister may perform differently under different conditions. Other issues may be encountered towards the end of life (EOL) of the canister compared with the beginning of life (BOL), such as variability in the return force, which may degrade over time. Therefore the damping system is optionally configured such that the tolerances and variations in performance are accounted for in inhalers of embodiments of the present invention. Optionally the first time segment is in the range of about 0.05 to 2.00 seconds, optionally in the range of about 0.10 to 1.75 seconds, optionally in the range of about 0.20 to 1.50 seconds, optionally in the range of about 0.30 to 1.25 seconds, optionally in the range of about 0.40 to 1.20 seconds. Time segments within one or more of these ranges have been found to be suitable at accounting for variations in performance and also at accounting for tolerances and differences between canisters and batches of canisters etc. Optionally the first time segment is at least about 0.20 seconds, optionally at least about 0.30 seconds, optionally at least about 0.40 seconds. These minimum times have been found to be optimal for ensuring the entire dose in the valve is dispensed each actuation.

Optionally the second time segment is in the range of about 0.10 to 2.00 seconds, optionally in the range of about 0.30 to 1.80 seconds, optionally in the range of about 0.40 to 1.70 seconds, optionally in the range of about 0.60 to 1.60 seconds, optionally in the range of about 0.80 to 1.50 seconds, optionally in the range of about 1.00 to 1.40 seconds. Again, time segments within one or more of these ranges have been found to be suitable at accounting for variations in performance and also at accounting for tolerances and differences between canisters and batches of canisters etc. Optionally the second time segment is less than about 2.0 seconds, optionally less than about 1.75 seconds, optionally less than about 1.50 seconds, optionally less than about 1.25 seconds, optionally about 1.20 seconds. These maximum times have been found to be optimal for ensuring the valve refills quickly and fully. As discussed above, it is thought to be particularly advantageous for the valve to be refilled fully whist the canister is held in a generally upright position, i.e. within a time frame of use by the user where the inhaler has not yet been removed from the user's mouth. Optionally the first time segment combined with the second time segment is a total time of less than about 2.5 seconds, optionally less than about 2.00 seconds, optionally less than about 1.75 seconds, optionally less than about 1.50 seconds. This provides a sufficient time for the valve to dispense and refill but is not so long as to adversely affect the quality of valve refill or to allow the user to significantly reposition the inhaler from the upright position in which it is used.

As discussed above, the inhaler comprises a damping system to provide the damped movement during the predetermined time period. Optionally the damping system comprises a rotary damper. Such dampers are available and perform reliably over multiple uses and are suited for use in embodiments of the present invention. Examples of such devices are rotary dampers as sold by ACE Controls International/Inc. or ACE Stoßdämpfer GmbH, etc.

Optionally the damping system comprises a rod, the rod coupled with a shaft of the rotary damper such that the rod rotates with the shaft, the rod rotation being controlled by the shaft rotation in at least a first direction of rotation. Thus movement of the rod is controlled by the damper. Optionally the rod is moveable relative to the shaft in an axial direction. Optionally the moving component comprises a cam follower and the rod comprises a cam track for receiving the cam follower, the cam track and the cam follower being configured such that the cam follower abuts an edge of the cam track and applies an axial moving force to the rod when the moving component moves from the first position to the second position. Thus a mechanical arrangement is provided in which the rod can move rotationally and/or axially in at least one and optionally two directions. Optionally the cam track and the cam follower are configured such that the axial moving force applied by the cam follower to the edge of the cam track axially moves the rod in a direction away from the shaft and the rod thereby applies a driving force to the canister to drive the canister from the rest position to at least the actuating position. Optionally the cam track comprises at least a first section and a second section, the first section being substantially aligned with the axis of the rod and the second section being curved about a portion of the outer surface of the rod in a direction substantially away from the first section of the track. Thus the two speeds of movement of the rod are provided. The first section of track is configured to allow axial movement of the rod relative to the cam follower and the second section of the track is configured to allow axial and rotational movement of the rod relative to the cam follower. Rotational movement of the rod is damped by the rotational damper and the axial movement of the rod is not damped by the rotational damper so, for example, the combined rotational and axial movement of the rod is controlled and slower and when the cam follower reaches the axial section of the track, more rapid movement of the rod in the axial direction is enabled. Optionally the second section of the track is substantially helical about the portion of the outer surface of the rod. This provides a smooth and controlled movement of the cam follower. Optionally, for balance and improved control, the rod comprises a pair of cam tracks diametrically opposed on the rod outer surface, optionally wherein the second sections of the cam tracks are helical and the helices are either both right-handed or both left-handed.

As discussed above, optionally the cam track is configured such that a first section of the cam track is configured such that the damping system enables the canister to automatically return from the actuating position to the rest position initially at a first speed and is further configured such that the damping system enables the canister to automatically return from the actuating position to the rest position at a second speed at a later time within the predetermined time period. This enables efficient dose dispensing and refill of the canister valve within an appropriate time. In alternative embodiments, as the yoke has not reached its stop position abutting the portions of the cap when the canister has reached its actuating position, the cam track is configured such that the damping system enables the yoke to continue to move and the canister is maintained in its actuating position during yoke movement, and the cam track is further configured such that the damping system enables the canister to automatically return from the actuating position to the rest position at a later time within the predetermined time period, after the yoke movement has ceased. This enables efficient dose dispensing and refill of the canister valve within an appropriate time, Prior to activation of the inhaler, the inhaler may be held in a closed configuration for many hours and may only be used once or twice a day, for example. Therefore it is helpful in some embodiments to relieve the loading of the biasing means to reduce or avoid stresses on certain components of the inhaler. Optionally the inhaler further comprises a load-relieving mechanism configured to support at least one of the moving component and at least a part of the damping system in a spaced apart position in which the moving component and/or the part of the damping system is not in contact with the canister, when the canister is received in the inhaler body. Thus the stresses that might otherwise be imparted by the loaded biasing means to components of the inhaler are reduced or otherwise alleviated. Optionally the load-relieving mechanism is configured to release the moving component and/or the part of the damping system to thereby bring the moving component and/or the part of the damping system, under the load of the biasing means, into contact with the canister, when the canister is received in the inhaler body. This may be directly or indirectly via another component or mechanism of the inhaler.

Optionally the load-relieving mechanism is configured to release the moving component to thereby bring the rod of the damping system, under the load of the biasing means, into contact with the canister, when the canister is received in the inhaler body, such that the rod is enabled to apply the driving force to the canister to drive the canister from the rest position to at least the actuating position. Thus the rod only contacts the canister when the biasing force is about to be applied to the canister and reduces the likelihood of wear of the rod when the inhaler is not about to be used. Optionally the load-relieving mechanism is configured such that the cam follower does not abut the edge of the cam track when the load-relieving mechanism is supporting the moving component and/or the part of the damping system. Again this alleviates any stresses or wear that might otherwise occur, for example between the cam follower and the edge of the track.

In alternative embodiments of the present invention, the damping system comprises a linear damper. All the above embodiments and optional features are applicable to this alternative embodiment where compatible and appropriate and are not intended to be limited only to the embodiment comprising a rotary damper. In the alternative embodiment, the linear damper comprises a generally cylindrical reservoir containing an incompressible fluid and an elongate piston arranged coaxially through the reservoir and protruding at both a proximal and a distal end from the reservoir, relative to the canister when received in the inhaler body, the piston configured to slide linearly back and forth through the reservoir along the co-axis. The piston performs effectively the same function as the rod of the rotary damper embodiment and the description of features and functions of the rod discussed throughout the specification is also applicable where compatible to the piston.

As discussed above, the piston is configured to slide back and forth through the reservoir, thus the protruding ends move in and out of the reservoir. To seal the piston, particularly as its ends move into and out of the reservoir, optionally the linear damper further comprises a lower seal for sealing the proximal end of the piston relative to the reservoir and an upper seal for sealing the distal end of the piston relative to the reservoir, such that fluid egress from the reservoir is substantially minimised or prevented.

As discussed above in relation to the rotary damper embodiment, optionally the linear (axial) movement of the rod, and in this embodiment, of the piston, can occur at two speeds, one faster than the other. In this embodiment, the damper is optionally configured in this manner. The reservoir of the linear damper comprises a proximal chamber having a first diameter and a distal chamber having a second diameter, the first diameter being less than the second diameter and optionally further comprising an intermediate section between the proximal and distal chambers, the intermediate section having a diameter that increases from a proximal end adjacent the reservoir proximal chamber to a distal end adjacent the reservoir distal chamber. The linear damper optionally further comprises a piston seal inside the reservoir, the piston seal surrounding the piston and affixed thereto and having a diameter such that it seals against the inside of the proximal chamber of the reservoir of the linear damper. As the proximal chamber has a smaller diameter, the piston seal optionally does not contact and/or seal against the larger diameter distal chamber or may contact the walls of the distal chamber but does not completely seal against the walls and therefore allows fluid flow to at least some degree around the outside of the seal as discussed further below.

When the piston seal is located in the proximal chamber and seals against the inside walls of the chamber, fluid flow is restricted or prevented between the proximal and distal chambers by the piston seal. However in order for the piston to be able to move, at least at a slow rate, some fluid flow between the chambers is required. Therefore the piston optionally comprises a fluid flow channel, the fluid flow channel having an inlet beyond the proximal end of the piston seal and an outlet beyond the distal end of the piston seal and configured such that fluid may flow between the proximal chamber and the distal chamber even when the piston seal is positioned so as to fluidly isolate the proximal chamber from the distal chamber. Fluid flow between the chambers is regulated by the configuration of the channel (e.g. its diameter and inlet/outlet sizes), therefore movement of the piston, particularly the rate of movement of the piston, is controlled, at least until the piston seal moves (with movement of the piston in the distal direction) from the proximal chamber and into the distal chamber.

Similar to the rotary damper embodiment, the linear damper is coupled to the moving member such that movement of the moving component from the first position to the second position, when the biasing means is released from the loaded configuration, drives the piston proximally the piston thereby applying a driving force to the canister to drive the canister from the rest position to at least the actuating position. Optionally the channel of the piston is configured such that fluid flow therethrough is restricted to thereby minimise or prevent axial movement of the piston in the distal direction relative to the reservoir until the canister has reached at least the actuating position. Therefore under the significant load when the biasing means is released, fluid flow through the channel is effectively prevented or at least minimised such that the piston is fixed relative to moving member during driving of the canister from the rest position to at least the actuating position (which might occur in, for example, a very short time period such as 10 ms, optionally 8 ms, optionally 6 ms, optionally 5 ms, optionally 4 ms, optionally 3 ms). However, after this initial rapid movement, fluid flow through the channel is possible. Optionally the channel of the piston is configured such that fluid flows therethrough at a restricted rate from the proximal chamber to the distal chamber, thereby enabling the piston to move axially in the distal direction at a controlled rate. Optionally the piston is configured such that a driving force from a return spring of the canister is sufficient to drive the piston axially in the distal direction, optionally wherein the return spring of the canister is further assisted by at least one additional return spring of the inhaler. Canisters for use in such inhalers according to embodiments of the present invention comprise a spring configured to return the valve (which is compressed into the canister to dispense a dose) to its rest position, in which the valve (typically a metering valve with a chamber sized to a desired dose level) is refilled from the main reservoir of the canister ready to dispense the next dose. The force of this spring is typically more than sufficient to return the canister to its rest state and therefore is able to push the canister in the distal direction and to push the piston axially in the distal direction. Fluid flow through the channel controls the rate at which the piston moves and thus the rate at which the canister valve moves to its rest position. Optionally to assist the valve spring of the canister, one or more return springs are provided in the inhaler, that are compressed when the inhaler is fired and unload thereafter to push the canister in the distal direction.

As discussed previously, the linear damper is optionally configured such that axial movement of the piston in the distal direction is for the first time segment at a first speed determined by the piston channel followed in the second time segment at a second speed when the piston seal passes into the distal chamber and thereby fluid flows around the outside of the piston seal. Optionally the piston seal comprises a lip seal comprising concentric rings separated by a thinner section, the lip seal configured to flex radially inwardly or outwardly under fluid pressure to allow or minimise fluid flow around the outside of the piston seal. Therefore as the piston seal moves from the proximal chamber to the distal chamber, the outer ring can flex radially towards the inner ring(s) under fluid pressure to further open the channel around the outside of the seal and conversely as the piston seal moves from the distal chamber to the proximal chamber, the outer ring can flex radially away from the inner ring(s) under fluid pressure (particularly in the gap between the rings) to further improve the seal between the piston seal and the distal chamber walls and to minimise or prevent fluid flow around the outside of the seal.

A further advantage of certain embodiments of the linear damper described herein is the insensitivity of the linear damper to the operating conditions and particularly to the operating temperature. For example, in lower (cold) temperatures, the seal is stiffer, so bypass occurs earlier and this compensates for some of the increased viscosity of the damping fluid due to the cold temperature. Conversely, in higher (hot) temperatures the seal will be more flexible, so bypass occurs later, which compensates for and minimises the effect of the reduced viscosity of the damping fluid.

As discussed above in relation to the rotary damper embodiment, the inhaler of this embodiment optionally further comprises a load-relieving mechanism configured to support at least one of the moving component and at least a part of the damping system in a spaced apart position in which the moving component and/or the part of the damping system is not in contact with the canister, when the canister is received in the inhaler body. Thus the stresses that might otherwise be imparted by the loaded biasing means to components of the inhaler are reduced or otherwise alleviated. Optionally the load-relieving mechanism is configured to release the moving component and/or the part of the damping system to thereby bring the moving component and/or the part of the damping system, under the load of the biasing means, into contact with the canister, when the canister is received in the inhaler body. This may be directly or indirectly via another component or mechanism of the inhaler.

Optionally the load-relieving mechanism is configured to release the moving component to thereby bring the proximal end of the piston of the damping system, under the load of the biasing means, into contact with the canister, when the canister is received in the inhaler body, such that the piston is enabled to apply the driving force to the canister to drive the canister from the rest position to at least the actuating position. Thus the piston only contacts the canister when the biasing force is about to be applied to the canister and reduces the likelihood of wear of the piston when the inhaler is not about to be used.

As discussed above, the reservoir of the damper contains an incompressible fluid. Optionally the incompressible fluid comprises silicone oil, optionally medical grade silicone oil and/or optionally silicone oil with a viscosity of about 5000 cSt, optionally about 4500 cSt, optionally about 4000 cSt, optionally about 3500 cSt, optionally about 3000 cSt, optionally about 2500 cSt, optionally about 2000 cSt, optionally about 1500 cSt, optionally about 1000 cSt, optionally about 750 cSt, optionally about 500 cSt, optionally about 250 cSt, optionally about 200 cSt. The fluid viscosity and other properties are optimised to the specific configuration of the linear damper.

In further alternative embodiments of the present invention, the damping system comprises an alternative linear damper. All the above embodiments and optional features are applicable to this alternative embodiment where compatible and appropriate and are not intended to be limited only to the embodiment comprising a rotary damper or another linear damper. In the alternative embodiment, the linear damper is a hydraulic damper comprising a generally cylindrical reservoir containing an incompressible fluid and an elongate piston arranged coaxially with the reservoir and protruding at proximal end from the reservoir, relative to the canister when received in the inhaler body, the piston configured to slide linearly back and forth into and out of the reservoir along the co-axis. Optionally the linear damper further comprises an elongate piston arranged coaxially with the reservoir and protruding at distal end from the reservoir, the elongate piston comprising a sealing section at a proximal end thereof, wherein the reservoir comprises a distal chamber and a proximal chamber that are fluidly isolated by the sealing section. Optionally the sealing section comprises a channel therethrough configured to allow fluid flow between the distal chamber and the proximal chamber such that movement of the sealing section is enabled and thus movement of the pistons is also enabled.

As is readily appreciable, the linear damper of this embodiment is similar in many aspects to the linear damper of the other embodiment (and has many similar features and functions as the rotary damper embodiment) and therefore all features and functions discussed in relation to the other embodiments are envisaged as part of this embodiment also where compatible.

Furthermore, all embodiments have at least some features in common, for example the biasing means. Optionally the biasing means comprises a spring, the spring optionally having a spring force when compressed in the range of about 45 to 85 N, optionally in the range of about 50 to 80 N, optionally in the range of about 55 to 75 N, optionally in the range of about 55 to 65 N.

Optionally the inhaler further comprises a breath-triggering mechanism configured to hold the biasing means in the loaded configuration and to release the biasing means to move the moving component from the first position to the second position in response to airflow in the inhaler. Optionally the breath-triggering mechanism comprises a vane configured to pivot in response to airflow in the inhaler and a latch configured to release the biasing means when the vane pivots. This embodiment is advantageous as the user of the inhaler need only inhale and the inhaler automatically triggers the dispensing of a dose and then resets the canister, all without further user interaction being required and all within a short period of time, ensuring efficient and reliable performance of the inhaler, particularly on refilling of the valve in preparation for the subsequent dose, as will be described further below.

From a further broad aspect, there is provided a method of dispensing medicament from an inhaler, the method comprising releasing a biasing means of a drive mechanism of the inhaler from a loaded configuration, moving, by the released biasing means, a moving component of the drive mechanism from a first position to a second position to drive a canister, received in a body of the inhaler, from a rest position, in which a valve of the canister is closed, to at least an actuating position, in which the valve is open, automatically returning the canister from the actuating position to the rest position within a predetermined time period measured from the release of the biasing means from the loaded configuration, the automatic return of the canister being regulated by a return mechanism comprising a damping system, and resetting the drive mechanism with a resetting mechanism that moves the moving component from the second position to the first position and reloads the biasing means to the loaded configuration. Optionally the step of automatically returning the canister within the predetermined time period comprises automatically returning the canister during a first time segment during which movement of the canister from the actuating position to the rest position is slower than during a second time segment. Optionally the second time segment immediately follows the first time segment. Optionally the first time segment is in the range of about 0.05 to 2.00 seconds, optionally in the range of about 0.10 to 1.75 seconds, optionally in the range of about 0.20 to 1.50 seconds, optionally in the range of about 0.30 to 1.25 seconds, optionally in the range of about 0.40 to 1.20 seconds. Optionally the first time segment is at least about 0.20 secs, optionally at least about 0.30 seconds, optionally at least about 0.40 seconds. Optionally the second time segment is in the range of about 0.10 to 2.00 seconds, optionally in the range of about 0.30 to 1.80 seconds, optionally in the range of about 0.40 to 1.70 seconds, optionally in the range of about 0.60 to 1.60 seconds, optionally in the range of about 0.80 to 1.50 seconds, optionally in the range of about 1.00 to 1.40 seconds. Optionally the second time segment is less than about 2.0 seconds, optionally less than about 1.75 seconds, optionally less than about 1.50 seconds, optionally less than about 1.25 seconds, optionally about 1.20 seconds. Optionally the first time segment combined with the second time segment is a total time of less than about 2.5 seconds, optionally less than about 2.00 seconds, optionally less than about 1.75 seconds, optionally less than about 1.50 seconds.

Optionally the damping system comprises a rotary damper. Rotary dampers are known in the art and are configured so as to have a torque that must be overcome and by which the rate of rotation of the damper is controlled. Optionally the damping system further comprises a rod, the rod coupled with a shaft of the rotary damper and wherein the rod rotates with the shaft, the rod rotation being controlled by the shaft rotation in at least a first direction of rotation. Optionally the rod moves relative to the shaft in an axial direction. Optionally the moving component comprises a cam follower and the rod comprises a cam track for receiving the cam follower, the cam follower abutting an edge of the cam track and applying an axial moving force to the rod when the moving component moves from the first position to the second position. Optionally the axial moving force applied by the cam follower to the edge of the cam track axially moves the rod in a direction away from the shaft and the rod thereby applies a driving force to the canister to drive the canister from the rest position to at least the actuating position. Optionally the cam track comprises at least a first section and a second section, the first section being substantially aligned with the axis of the rod and the second section being curved about a portion of the outer surface of the rod in a direction substantially away from the first section of the track. Optionally the first section of track allows axial movement of the rod relative to the cam follower and the second section of the track allows axial and rotational movement of the rod relative to the cam follower.

Optionally the rotational damper damps the rotational movement of the rod but not the axial movement of the rod. Optionally the second section of the track is substantially helical about the portion of the outer surface of the rod. Optionally the rod comprises a pair of cam tracks diametrically opposed on the rod outer surface, optionally wherein the second sections of the cam tracks are helical and the helices are either both right handed or both left-handed.

Optionally the canister automatically returns from the actuating position to the rest position initially at a first speed along a first section of the cam track and automatically returns from the actuating position to the rest position at a second speed at a later time along a second section of the cam track within the predetermined time period. Optionally, the first speed is substantially zero, i.e. the canister does not move initially, but returns from the actuating position to the rest position at a later time along a second section of the cam track within the predetermined time period.

Optionally the method further comprises supporting at least one of the moving component and at least a part of the damping system in a spaced apart position by a load relieving mechanism, the moving component and/or the part of the damping system not directly contacting the canister when supported by the load relieving mechanism.

Optionally the method further comprises releasing the moving component and/or the part of the damping system to thereby bring the moving component and/or the part of the damping system, under the load of the biasing means, into contact with the canister. Optionally the load-relieving mechanism releases the moving component to thereby bring the rod of the damping system, under the load of the biasing means, into contact with the canister, enabling the rod to apply the driving force to the canister and driving the canister from the rest position to at least the actuating position. Optionally the cam follower does not abut the edge of the cam track when the load-relieving mechanism supports the moving component and/or the part of the damping system.

Optionally the damping system comprises a linear damper. Optionally the linear damper comprises a generally cylindrical reservoir containing an incompressible fluid and an elongate piston arranged coaxially through the reservoir and protruding at both a proximal and a distal end from the reservoir, relative to the canister when received in the inhaler body, wherein the piston slides linearly back and forth through the reservoir along the co-axis. Optionally the linear damper further comprises a lower seal that seals the proximal end of the piston relative to the reservoir and an upper seal that seals the distal end of the piston relative to the reservoir, such that fluid egress from the reservoir is substantially minimised or prevented. Optionally the reservoir of the linear damper comprises a proximal chamber having a first diameter and a distal chamber having a second diameter, the first diameter being less than the second diameter and optionally further comprising an intermediate section between the proximal and distal chambers, the intermediate section having a diameter that increases from a proximal end adjacent the reservoir proximal chamber to a distal end adjacent the reservoir distal chamber. Optionally the linear damper further comprises a piston seal inside the reservoir, the piston seal surrounding the piston and affixed thereto and having a diameter such that it seals against the inside of the proximal chamber of the reservoir of the linear damper.

Optionally the piston comprises a fluid flow channel, the fluid flow channel having an inlet beyond the proximal end of the piston seal and an outlet beyond the distal end of the piston seal and wherein fluid flows between the proximal chamber and the distal chamber even when the piston seal is positioned so as to fluidly isolate the proximal chamber from the distal chamber. Optionally the step of moving the moving component from the first position to the second position further comprises driving the piston proximally and applying a driving force to the canister to drive the canister from the rest position to at least the actuating position. Optionally the method further comprises the step of restricting the fluid flow through the channel to thereby minimise or prevent axial movement of the piston in the distal direction relative to the reservoir until the canister has reached at least the actuating position. Optionally the channel of the piston is configured such that fluid flows therethrough at a restricted rate from the proximal chamber to the distal chamber, thereby enabling the piston to move axially in the distal direction.

Optionally the method further comprises the step of driving the piston axially in the distal direction with a driving force from a return spring of the canister, optionally further comprising the step of additionally driving the piston axially in the distal direction with a driving force from at least one return spring of the inhaler. Optionally the piston moves axially in the distal direction for the first time segment at a first speed determined by the piston channel followed in the second time segment at a second speed when the piston seal passes into the distal chamber and thereby fluid flows around the outside of the piston seal. Optionally the piston seal comprises a lip seal comprising concentric rings separated by a thinner section, wherein the lip seal flexes radially inwardly or outwardly under fluid pressure and allows or minimises fluid flow around the outside of the piston seal.

Optionally the method further comprises supporting at least one of the moving component and at least a part of the damping system in a spaced apart position by a load relieving mechanism, the moving component and/or the part of the damping system not directly contacting the canister when supported by the load relieving mechanism. Optionally the method further comprises releasing the moving component and/or the part of the damping system to thereby bring the moving component and/or the part of the damping system, under the load of the biasing means, into contact with the canister. Optionally the load-relieving mechanism releases the moving component to thereby bring the proximal end of the piston, under the load of the biasing means, into contact with the canister, enabling the piston to apply the driving force to the canister and driving the canister from the rest position to at least the actuating position.

Optionally the linear damper further comprises a piston seal inside the reservoir, the piston seal surrounding the piston and affixed thereto sealing against the inside of the reservoir of the linear damper. Optionally the piston comprises a fluid flow channel, the fluid flow channel having an inlet beyond the proximal end of the piston seal and an outlet beyond the distal end of the piston seal and wherein fluid flows between a proximal chamber of the reservoir and a distal chamber of the reservoir through the channel, the proximal and distal chambers fluidly isolated by the piston seal. For example, the fluid flow channel may be formed in a solid portion of the piston, some distance removed from the seal area.

Optionally the step of moving the moving component from the first position to the second position drives the piston proximally and the piston applies a driving force to the canister and drives the canister from the rest position to at least the actuating position.

Optionally the method further comprises the step of holding the biasing means in the loaded configuration with a breath-triggering mechanism that releases the biasing means in response to airflow in the inhaler. Optionally the method further comprises the step of pivoting a vane of the breath-triggering mechanism in response to airflow in the inhaler, the pivoting vane releasing a latch of the breath-triggering mechanism to release the biasing means.

BRIEF DESCRIPTION OF THE DRAWINGS

Preferred aspects and embodiments of the present invention will now be described, by way of example only, with reference to the accompanying drawings, in which:

FIG. 2 is a perspective view of a damping system in accordance with embodiments of the present invention;

FIG. 12 is a front view of a damping system in accordance with alternative embodiments of the present invention;

FIGS. 16A to 16E illustrate operation of the inhaler and damping system of the embodiments of FIGS. 12 to 15;

FIG. 19 is a plot showing actual operation of the inhaler and damping system of the embodiments of FIGS. 1 to 8;

DETAILED DESCRIPTION OF PREFERRED EMBODIMENTS

Inhalers and methods of operating inhalers in accordance with embodiments of the present invention are illustrated in the figures.

Figure 1A:
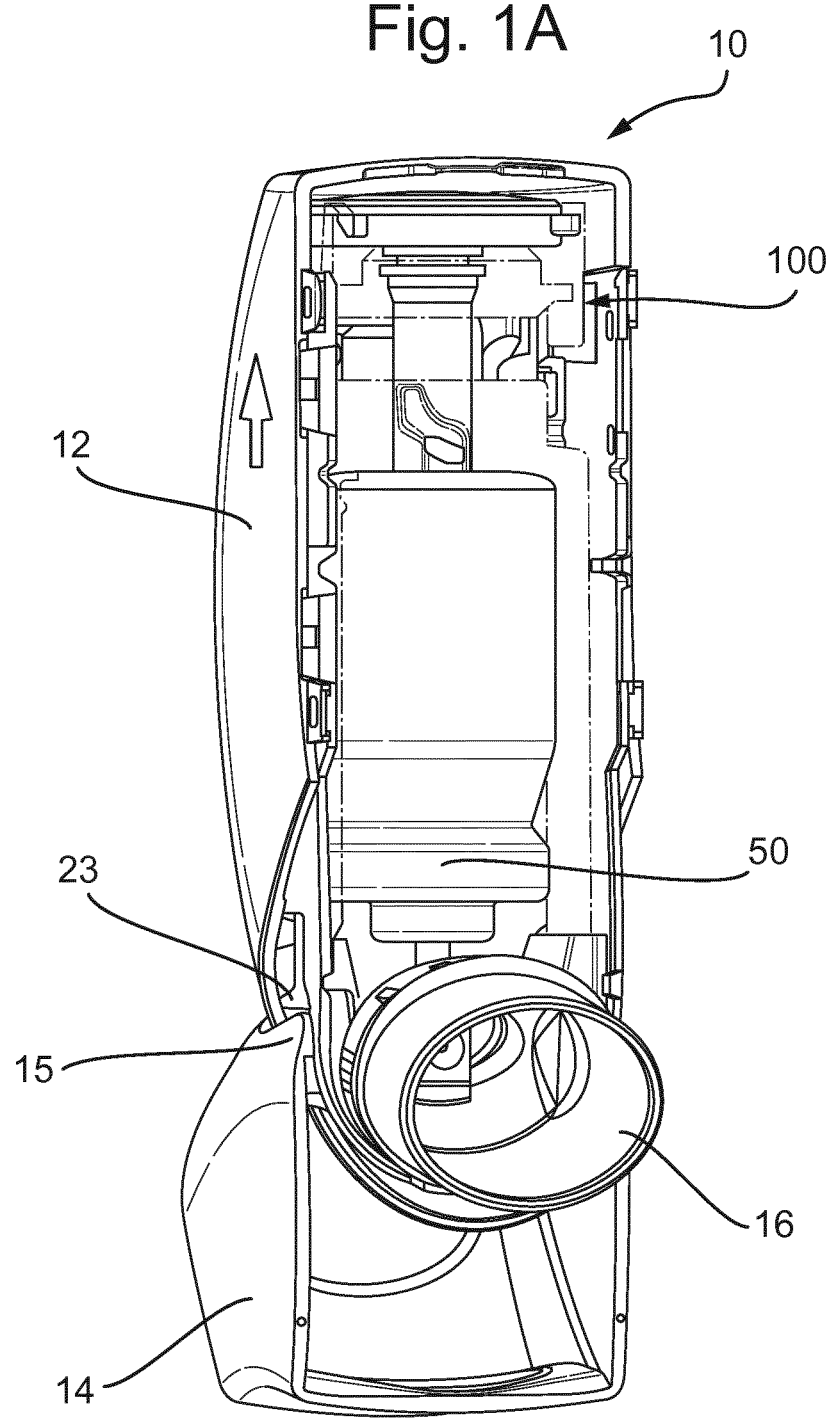
FIG. 1A is a perspective view of an inhaler in accordance with embodiments of the present invention and FIG. 1B is a cut-away version thereof.
Figure 1B:
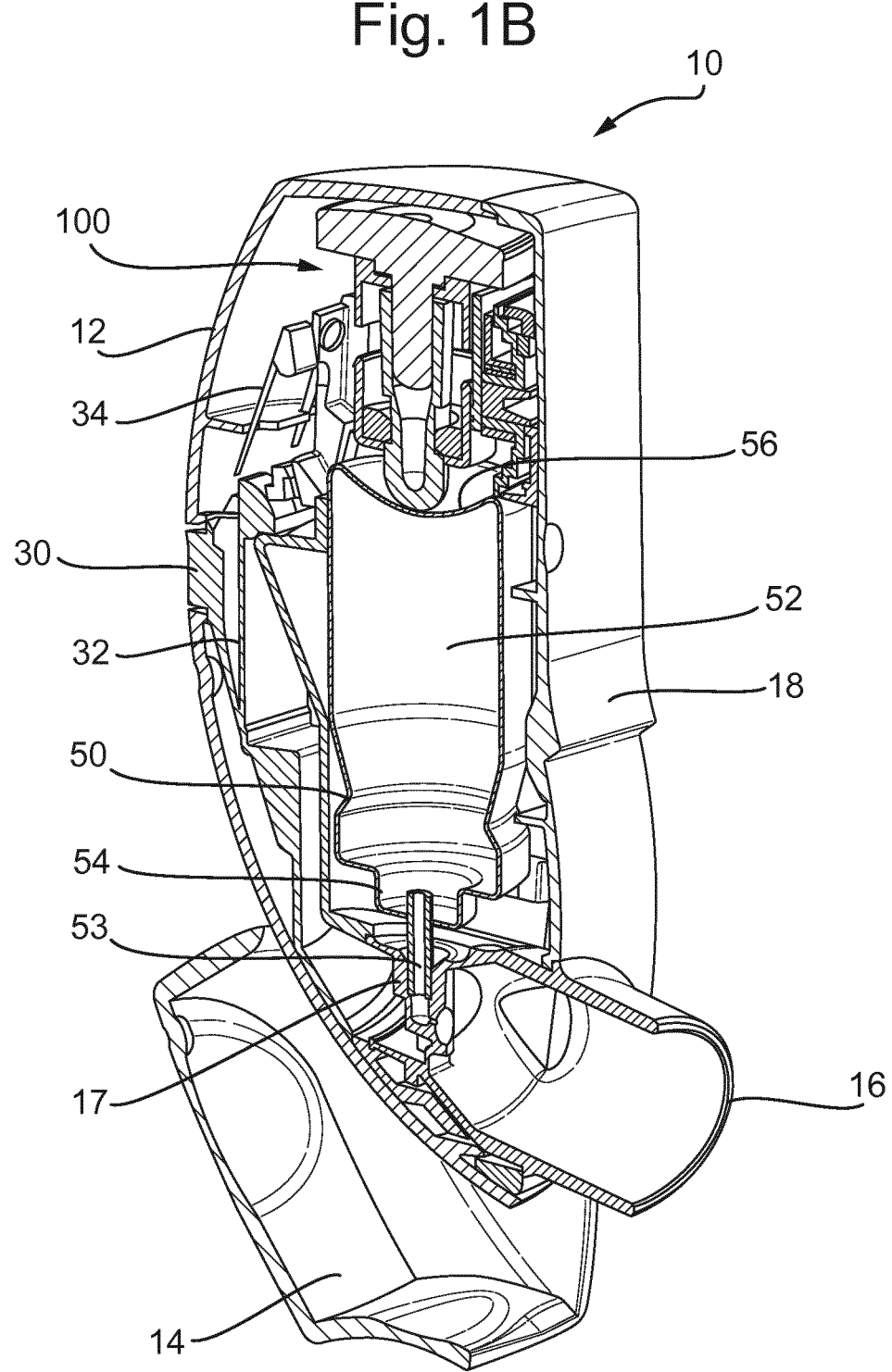
Figure 5A:
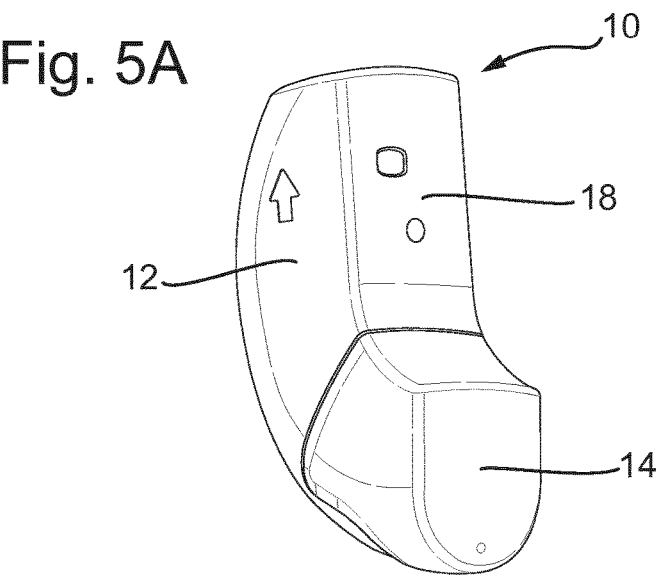
FIG. 5A is a perspective view of the inhaler of FIGS. 1 to 3 in a closed configuration and FIG. 5B is an exploded view of the inhaler of FIG. 5A.

Referring to FIG. 1, an inhaler 10 is shown, which in this illustration is a breath-triggered inhaler 10 with a breath-triggering mechanism 32, 34, as will be described in more detail later. FIG. 1A is a perspective view of the inhaler 10 and FIG. 1B is a cross-section of the inhaler 10, cut-away to show the inner components of the inhaler 10. The inhaler 10 has an outer housing or shell 12, which contains most of the components of the inhaler 10. At the base of the shell 12 there is a movable mouthpiece cover or cap 14 that pivots relative to the shell 12 to expose or cover the mouthpiece 16 of the inhaler 10. In combination with the front plate or fascia 18 of the inhaler 10, the shell 12 and cap 14 entirely enclose all the components of the inhaler 10 when in the closed configuration (as can be seen in FIG. 5A for example).

Figure 3:
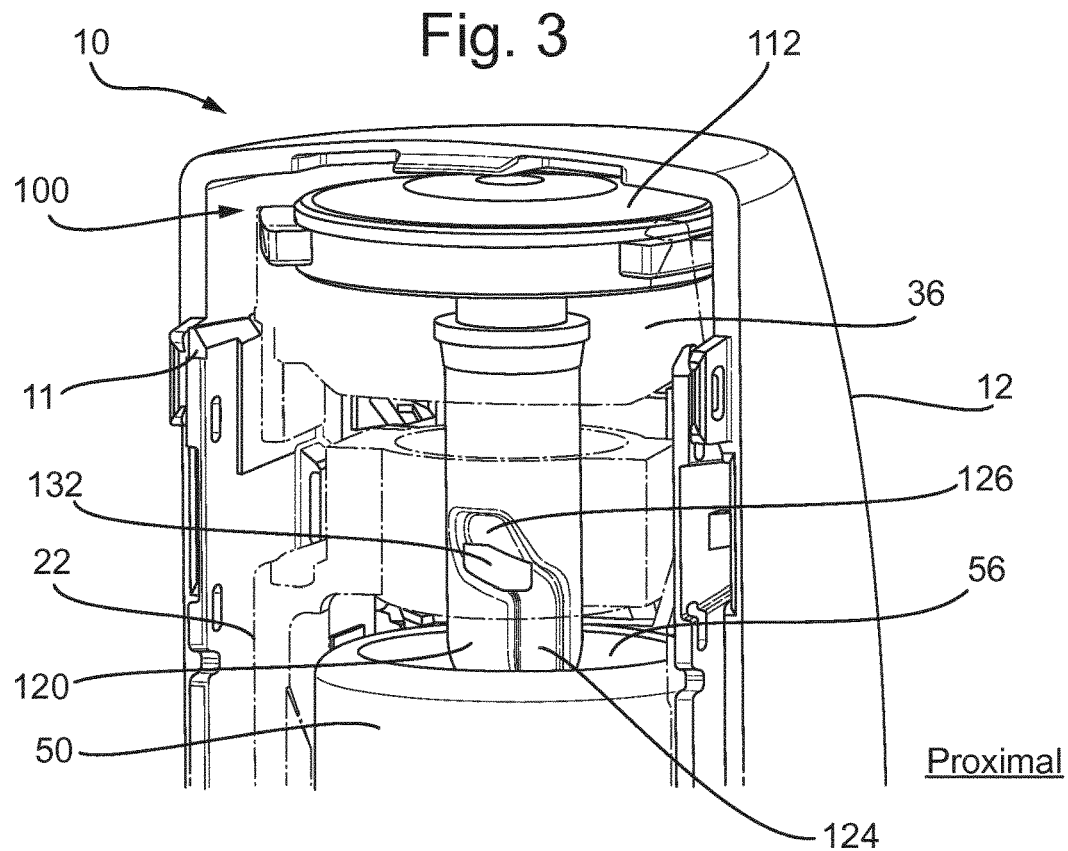
FIG. 3 is a perspective view of a portion of the inhaler system of FIG. 1, illustrating the damping system in situ.

Inside the inhaler 10 there is a canister 50 with a reservoir 52 that contains medicament. A valve 54 of the canister 50 has a metering chamber for metering a single dose of the medicament, as is known in the art. To dispense a dose of medicament, the canister 50 is compressed and a stem 53 of the valve 54, which sits in a seat 17 of the mouthpiece 16, is forced into the canister 50, which opens the valve 54 and the pressurised dose of medicament is expelled into the mouthpiece 16 for inhalation by the user. The canister 50 is compressed by a main spring 20 (shown in the exploded view of the inhaler 10 of FIG. 5B), which is held in a loaded position above the canister 50 and is released so as to expand downwardly in the inhaler 10. It is to be noted here that relative terms such as upwardly, downwardly, laterally, top, bottom, upper, lower, etc., are for ease of reference only and are not intended to be limiting in any way and are used in relation to the inhaler 10 being in its upright position for inhalation (as it is shown in most of the figures). The released spring 20 pushes downwardly on a yoke 22 of the inhaler 10, which is best seen in FIG. 3 onwards as described further below. The yoke 22 is driven from its first, pre-fire position by the unloading spring 20 and moves rapidly to a second, fired position, which is determined by the lowermost portion of the yoke 22 coming into contact with another part of the inhaler 10. In the illustrated embodiment, the legs 25 of the yoke 22 have feet 23 (see FIG. 7 for example) and these feet 23 are driven into contact with bearing surfaces 15 of the opened cap 14 to halt the downward movement of the yoke 22. In alternative arrangements, a different stop means may be provided, for example a stop on the chassis (not shown).

Typically the spring 20 has a force in the range of about 45 to 85 N when compressed and therefore drives the yoke 22 rapidly to its fired position when released, for example in just a few milliseconds, such as around 4 ms. As the yoke 22 moves to its fired position, it interacts with a damping system 100 of the inhaler 10, driving a rod 120 of the damping system 100 downwardly as will be described in more detail with reference to FIG. 2 onwards. The rod 120 forces the canister 50 downwards with sufficient force to drive the valve stem 53, which is held in the seat 17 of the mouthpiece 16, into the canister 50 (so driving the canister from a rest position to an actuating position), thus opening the valve to allow the dose of medicament in the metering chamber of the valve 54 to be released into the mouthpiece 16.

In inhalers 10 known in the art, such as well-known pMDI Inhalers, it is known that a problem may arise if the valve 54 is reset whilst the inhaler is in a position other than being held upright. For example, in the arrangement shown in the figures, the valve 54 remains in its open position until the yoke 22 is pushed back to its first position, which also reloads the spring 20. This is achieved by the user of the inhaler 10 closing the cap 14. The bearing surfaces 15 of the cap 14 are cams that impart an upward force on the feet 23 of the yoke 22 when the cap 14 is rotated by the user to its closed position to cover the mouthpiece 16. A latch mechanism 34 then engages to hold the spring 20 in its compressed state ready for the next actuation. A problem with this arrangement is that the user might forget to close the cap 14 straight after use and it has been observed that in some cases, this can lead to the metering chamber of the valve 54 refilling less effectively. Even if the cap 14 is closed relatively quickly after using the inhaler 10, it is often the case that the user will remove the inhaler 10 from the dispensing position in which the inhaler 10 is generally upright, and close the cap 14 with the inhaler 10 in a different orientation, for example with the mouthpiece 16 facing upwards. It has recently been observed that orientation of the canister 50 when it is moving to its rest position (thereby refilling the valve 54) may also influence how well the valve 54 refills and may affect the quality of the next dose of medicament, since gravity might also affect filling of the valve 54, particularly towards the canister 50 end of life when the fluid level is lower.

Therefore the inhalers 10 according to embodiments of the present invention comprise a mechanism for automating closure of the valve 54 by returning the canister 50 to its rest position soon after the current dose has been dispensed, irrespective of whether the user closes the cap 14 straight after using the inhaler 10. Furthermore, the automated closure of the valve 54 occurs within a predetermined time period and is sufficiently soon after dispensing the dose that it is unlikely, or even not possible, that the user will have reoriented the inhaler 10 from its upright position (i.e. the closure of the valve 54 occurs quickly enough that the user will not have reacted to any significant extent before the valve 54 is closed and so the valve 54 will close whilst the user still has the inhaler 10 in its upright, in use, position). As illustrated in FIG. 1, the mechanism for automating resetting of the canister 50 and valve 54 comprises a damping system 100. FIG. 2 illustrates the main components of the damping system 100 isolated from the inhaler 10 for ease of reference. The damping system of this embodiment comprises a rotary damper 110, which has a top unit 112 and a shaft 114 protruding therefrom. Such rotary dampers 110 are available at the time of this filing, e.g. as sold by ACE Controls International/Inc., or ACE Stoßdämpfer GmbH, etc., therefore further detail is known to the skilled person. The rotary damper 110 controls (damps) rotational movement of components within the top unit 112 in at least one direction such that rotation of the shaft 114 is also controlled (damped) in at least one direction. Therefore forces acting on the shaft 114 will only rotate the shaft 114 at a speed determined by the top unit 112 as discussed further below.

Figure 4:
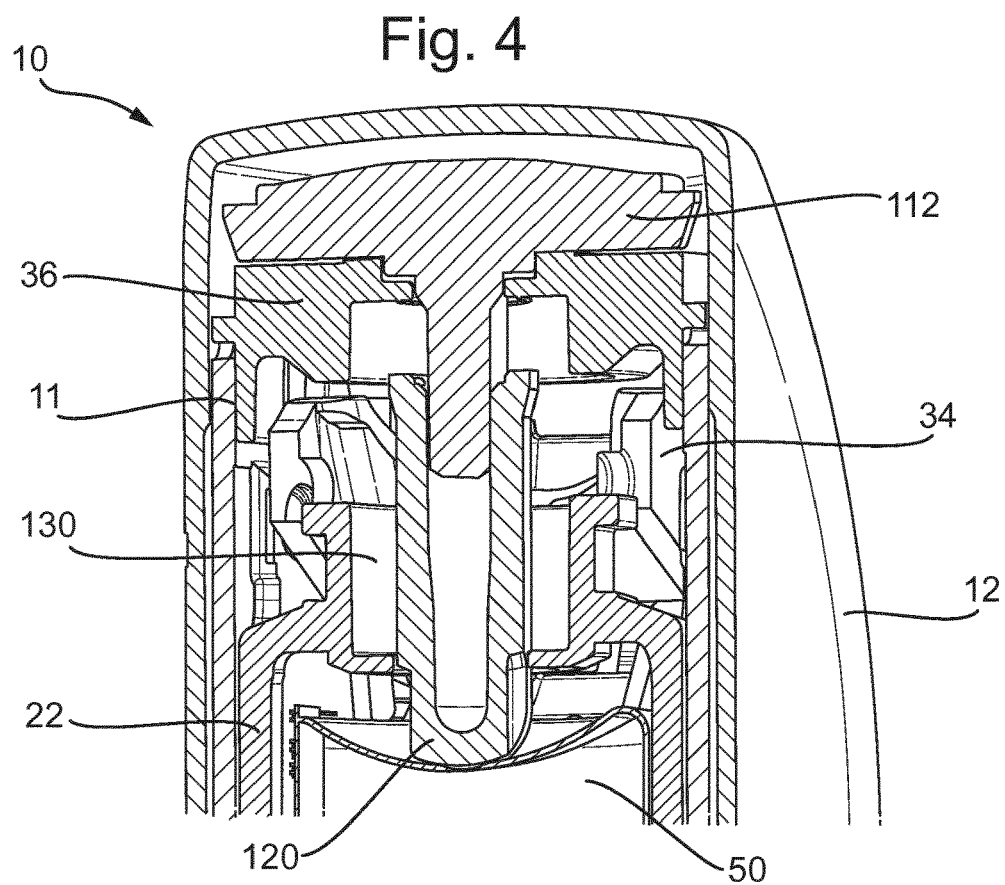
FIG. 4 is a cut-away version of FIG. 3, illustrating inner parts of the damping system.

The damping system 100 further comprises a rod 120. The rod 120 is generally elongate and has an inner bore 122 along its central axis for receiving the shaft 114 of the rotary damper 110 (as seen in FIGS. 2, 4 and 6 for example). The surface of the inner bore 122 has a profile configured to provide a locking fit with the shaft 114 such that the shaft 114 and the rod 120 are immovably fixed together in at least the direction of rotation about the rod 120 and shaft 114 central axes. For example in the FIG. 2 embodiment, the inner bore 122 comprises a Torx® interface, though other arrangements are within the scope of the invention. The surface of the inner bore 122 of the rod 120 does not prevent axial movement of the rod 120 relative to the damper shaft 114. Therefore the rod 120 is able to slide in a linear, axial direction up and down the shaft 114. For ease of reference, movement in an upward direction (referring to FIG. 1, when the inhaler 10 is upright as shown) will be defined as in the distal direction and movement in a downward direction will be defined as in the proximal direction (see also FIG. 3). So for the damping system 100 this is relative to the canister 50 (the top unit 112 being distal from the canister 50 compared with the rod 120, for example) or in general distal and proximal are defined relative to the mouthpiece 16.

Figure 6A:
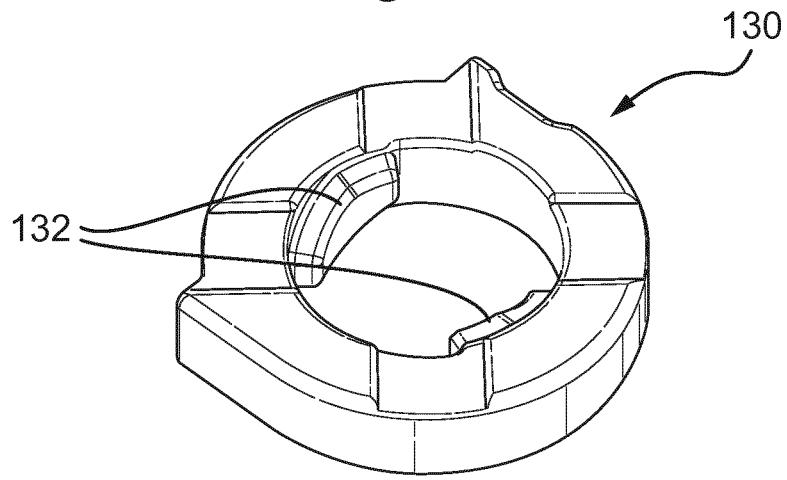
FIG. 6A is a perspective view of a yoke plate of the damping system of FIGS. 1 to 5 and FIG. 6B is a perspective view of a rod of the damping system of FIGS. 1 to 5.
Figure 6B:
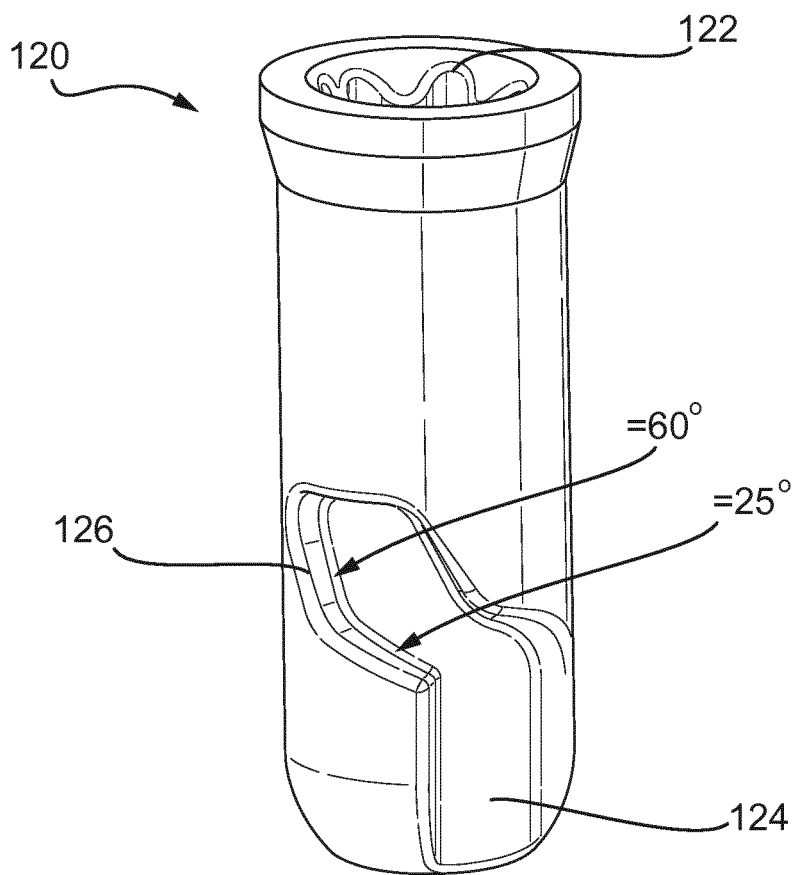
Figure 7A:
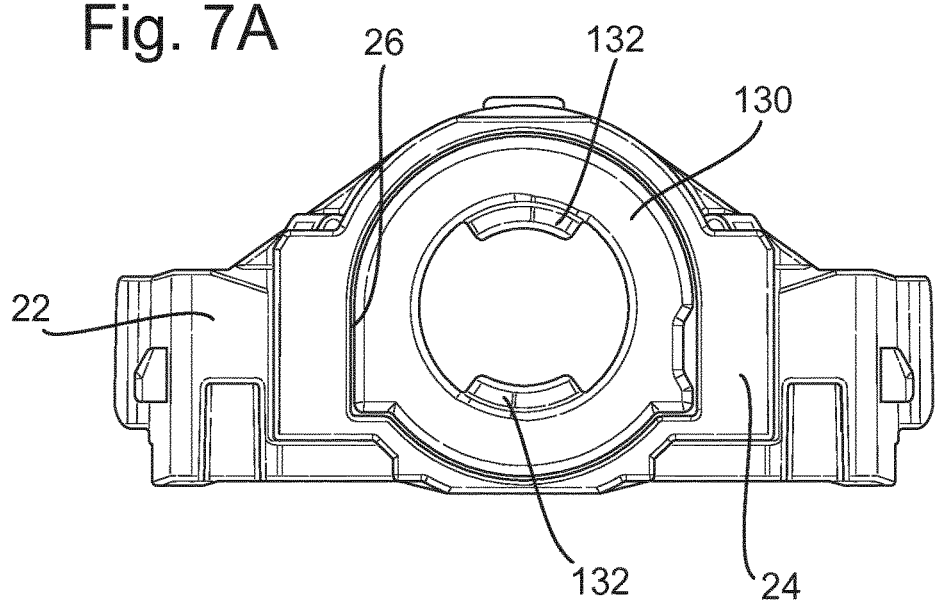
FIG. 7A is a top view of the yoke plate of FIG. 6A fixed in the yoke of the inhaler of FIGS. 1 to 5 and FIG. 7B is a perspective view of the yoke.
Figure 7B:
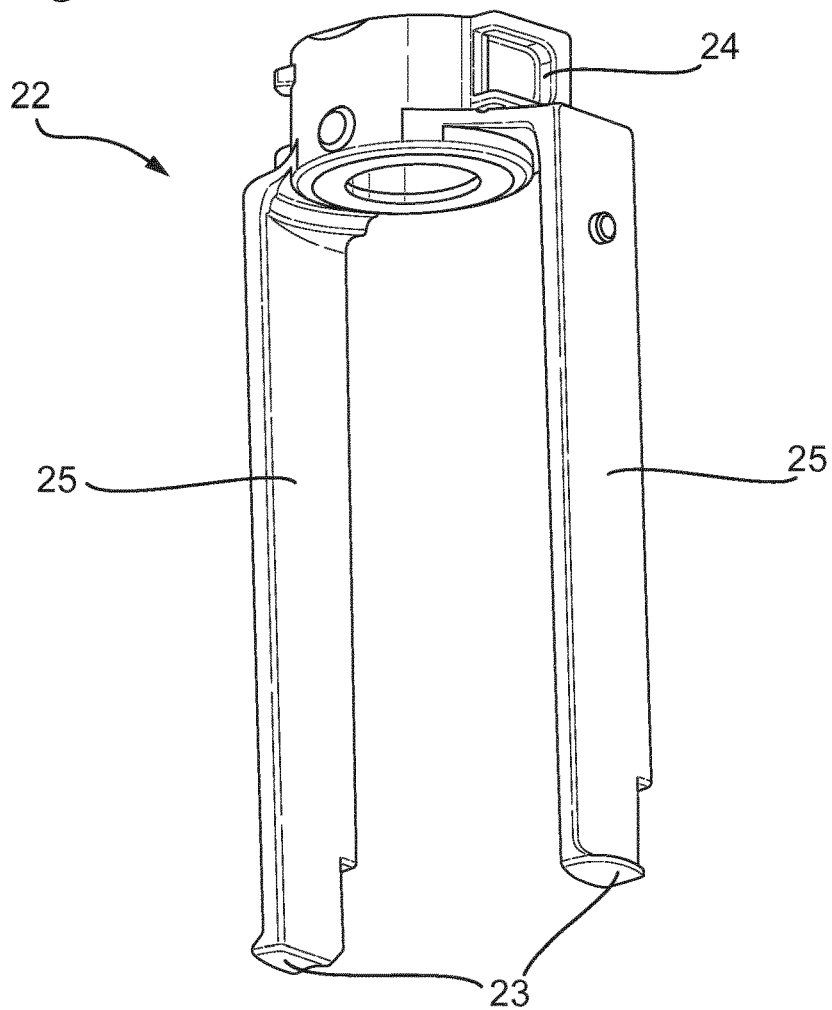

The damping system 100 further comprises a plate 130 and as seen in FIGS. 6A and 7A, the plate 130 is a ring having a pair of opposed teeth or lobes 132 protruding radially inward towards the centre of the ring. The teeth 132 act as cam followers and are configured to follow two sections of a cam track 124, 126 on an outer surface of the rod 120 (shown in FIG. 6B and discussed further below). The teeth 132 follow the track 124, 126 as the rod 120 rotates with the damper shaft 114 and also as it moves axially in the proximal/distal directions relative to the shaft 114. As the plate 130 is immovably fixed within the distal end of the yoke 22 (as seen in FIGS. 7A and 7B, being received in a cavity 26 within the yoke collar 24), the rod 120 is coupled to the yoke 22 via the teeth 132 of the yoke plate 130, as will be discussed further below. Whilst the yoke plate 130 is shown as a separate component in this embodiment, it is not necessary for it to be so and, for example, the yoke 22 may comprise the yoke plate 130 (i.e. they may be parts of the same component, integrally formed for example).

Figure 5B:
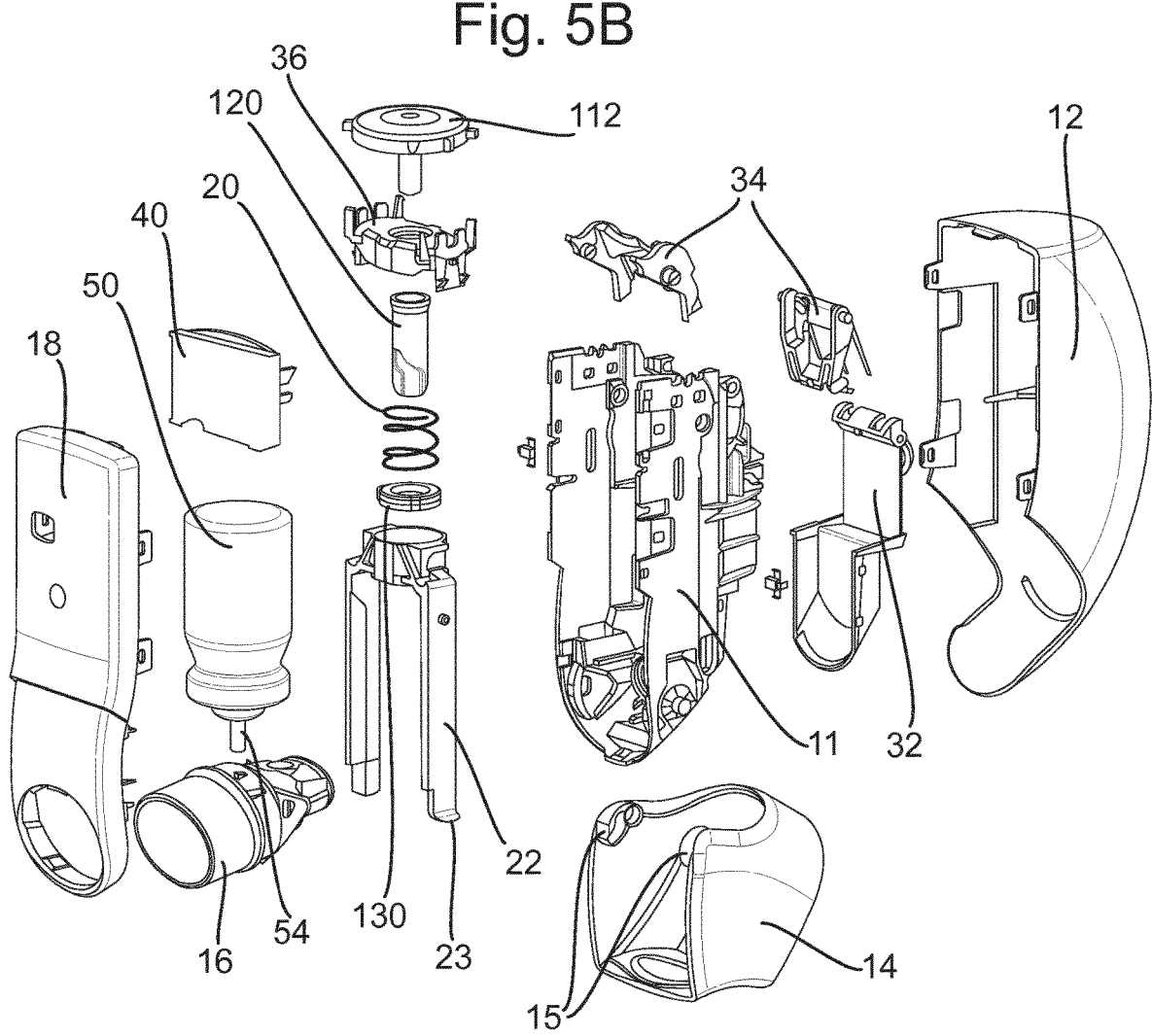

Referring to FIGS. 3 and 4, the damping system 100 is located in the inhaler 10 generally in the distal portion of the inhaler 10, above the canister 50. The damper top unit 112 is held in place by a cover 36 that is affixed to a chassis 11 that is configured to hold various parts of the inhaler 10 in position relative to the shell 12 or other parts of the inhaler 10. The rod 120 extends proximally from the top unit 112 and is received on the shaft 114 of the rotary damper 110. The rod 120 passes through the yoke plate 130 and the teeth 132 of the yoke plate 130 protrude into the tracks 124, 126 of the outer surface of the rod 120 (only one track 124, 126 is visible in the figures, but in this embodiment at least, a corresponding track is also provided on the outer surface of the rod 120 opposite the visible track 124, 126). The yoke plate 130 is fixed within the yoke 22 at a distal end thereof, in a collar 24 of the yoke 22 (see FIG. 7). The yoke 22 is guided by the chassis 11 but is able to move relative to the chassis 11 in both the distal and proximal directions. A main spring 20 (not shown in FIGS. 3 and 4; see FIGS. 5 and 8) is located between the cover 36 and the collar 24 of the yoke 22 and when released from a loaded configuration, the main spring 20 pushes downwardly on the yoke 22 and the yoke plate 130 to move the yoke 22 and yoke plate 130 in the proximal direction, as discussed further below. FIG. 5B shows the main components of the inhaler 10 in an exploded view for ease of reference to each component.

Figure 8A:
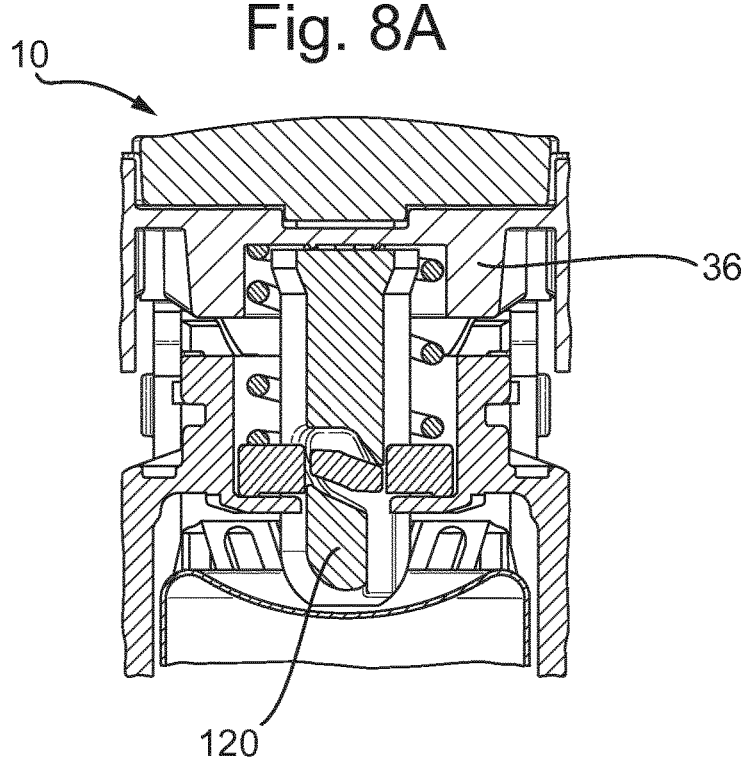
FIGS. 8A to 8E illustrate operation of the inhaler and damping system of the embodiments of FIGS. 1 to 7.

Operation of the inhaler 10 of this embodiment will now be described, with reference to FIGS. 8A to 8E. The figures focus on the damping system 100 of the inhaler 10 and its interaction with the surrounding components of the inhaler 10, particularly with the canister 50 and the yoke 22. FIG. 8A illustrates the inhaler 10 in its rest or closed position, in which the cap 14 is closed and the load of the compressed main spring 20 is supported or relieved as discussed below. This is the configuration in which the inhaler 10 will mostly be held as it is only when the inhaler 10 is to be used that the cap 14 will be opened. The closed inhaler 10 is illustrated in FIG. 5A. In this closed position, the yoke 22 is supported in its most distal position by the abutment of the feet 23 of the yoke 22 on the bearing surfaces 15 of the closed cap 14. The load of the main spring 20 is thus supported by the bearing surfaces 15 through the legs 25 of the yoke 22 and the yoke 22 is designed to withstand such a load. Other components of the inhaler 10 are relieved from any significant stresses whilst in this configuration and, for example, the rod 120 is raised above the canister 50 so it does not touch the canister base 56, the cam follower tooth 132 is not resting on the cam track 126, and the latch mechanism 34 of the breath-triggering mechanism 32, 34 (partially visible in FIG. 8 and also shown in FIGS. 4 and 5B) is not substantially holding the load of the spring 20.

Figure 8B:
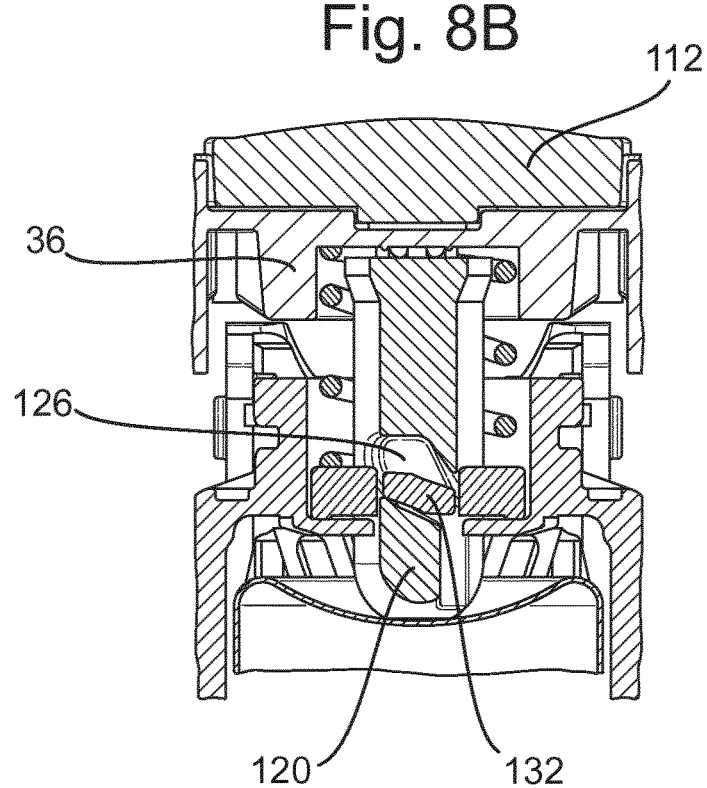

When the user wishes to inhale a dose of medicament from the inhaler 10, the first step is to open the cap 14 (although it should be noted that the user may need to shake the inhaler 10 before use, but further discussion of this requirement is not necessary as it is known in the art). Opening the cap 14 rotates the bearing surfaces 15 of the cap 14 and the yoke 22 moves slightly in the proximal direction under the force of the main spring 20, as shown in FIG. 8B. However the main spring 20 is not released in this pre-fire position because the latch 34 becomes engaged as the yoke 22 moves to this first, pre-fire position. Movement of the yoke 22 also moves the yoke plate 130, and the cam follower tooth 132 moves into contact with an edge of the cam track 126 and pushes the rod 120 into contact with the base 56 of the canister 50. In this configuration, the inhaler 10 is ready to fire to release a dose of medicament from the canister valve 54.

Figure 8C:
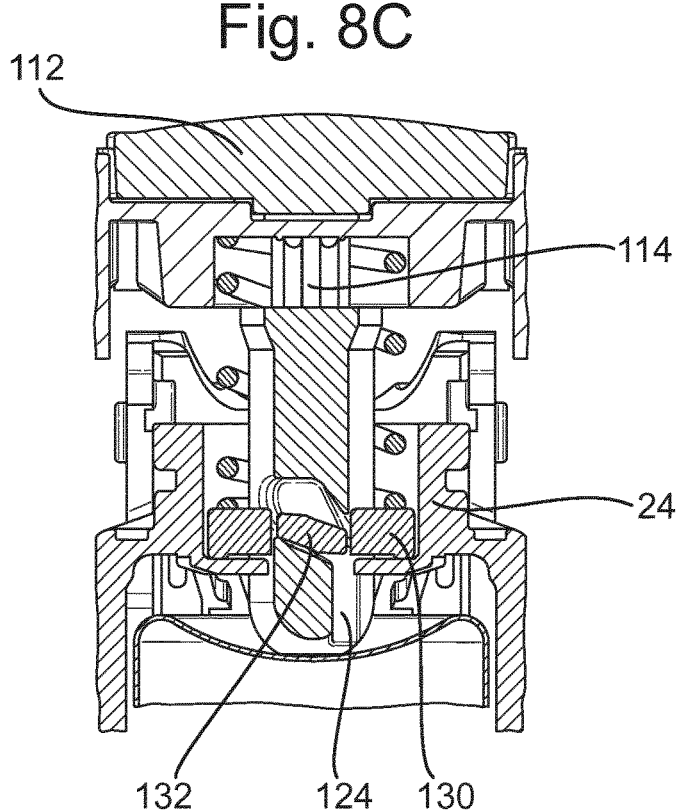

The inhaler 10 of these embodiments is a breath-triggered inhaler 10 and, when the user inhales through the mouthpiece 16, the airflow/pressure drop pivots a vane 32 (see FIGS. 1B and 5B) which releases the latch mechanism 34 and the main spring 20 releases much of its load and expands, pushing downwardly on the yoke 22 and yoke plate 130. The force of the spring 20 is large and the yoke 22 moves rapidly to a second, fired position, which is shown in FIG. 8C. Movement of the yoke 22 is stopped when the feet 23 of the yoke 22 hit the bearing surfaces 15 of the cap 14, in this embodiment, though other stop means may additionally or alternatively be provided. The rapid movement of the yoke 22 and yoke plate 130 forces the rod 120 to likewise push downwardly on the base 56 of the canister 50, driving the valve stem 53 of the canister 50 (which is held in the seat 17 of the mouthpiece 16) into the canister 50 and releasing a metered dose into the mouthpiece 16 for inhalation by the user. In this embodiment, the inhaler 10 is configured such that the feet 23 of the yoke 22 hit the bearing surfaces 15 of the cap 14 concurrently with the valve stem 53 reaching its furthest position inside the canister 50, i.e. when the canister 50 reaches its lowest position within the inhaler 10. The rod 120 is driven axially by the force of the cam follower tooth 132 pushing downwardly on the edge of the cam track 126; the rod 120 slides away from the top unit 112 of the damper 110 and along the shaft 114, but does not rotate because it is prevented from doing so by the configuration of the rotary damper 110 and the rapid movement of the cam follower tooth 132. As the rod 120 pushes downwardly on the canister 50, the spacing between the canister base 56 and the yoke collar 24 is maintained. As discussed above, movement of the components from the pre-fire position of FIG. 8B to the fired position of FIG. 8C is rapid and may occur in a very short time period, such as within a few milliseconds. Therefore the user receives a dose of medicament very quickly after they begin inhaling through the mouthpiece 16 of the inhaler 10. Whilst this embodiment is described in relation to the user triggering dispensing of a dose by inhalation through the mouthpiece 16, it is also possible for the user to fire a dose using a firing button 30, which has the same effect of pivoting the vane 32 but does so manually, which may be helpful, for example, for priming the device.

After the inhaler 10 has been fired, as shown in FIG. 8C, the damping system 100 is configured to release the downward force of the rod 120 on the base 56 of the canister 50 in a controlled manner so as to reset the canister 50 (moving it from the actuating position in FIG. 8C to the rest position of FIG. 8D) and moving the canister valve stem 53 to its closed position. The canister valve 54 refills its metering chamber as the valve stem 53 closes. It is important that the movement of the canister valve stem 53 relative to the canister 50 (i.e. the firing of the valve 54 and its subsequent refilling and resetting) is controlled over a predetermined period of time that is neither too short nor too long, to avoid the firing and/or refilling being insufficient or incomplete. This is discussed further below.

Figure 8D:
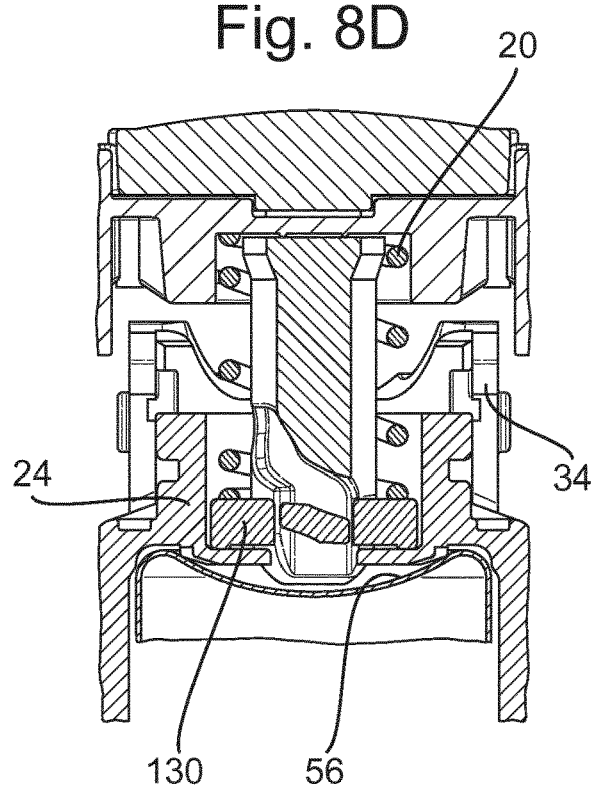
Figure 15A:
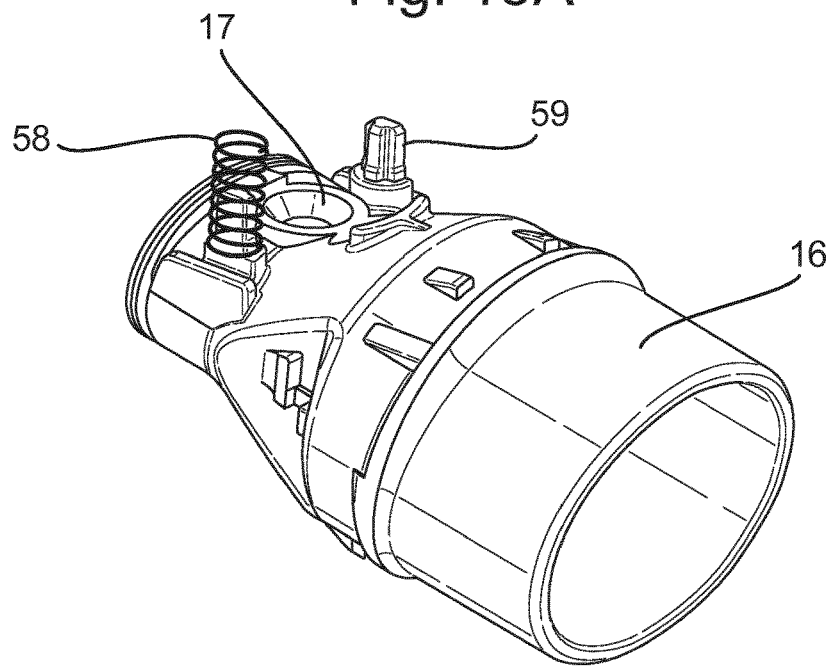
FIGS. 15A and 15B are perspective views of a mouthpiece in accordance with embodiments of the present invention on which supplementary canister return springs are provided.
Figure 15B:
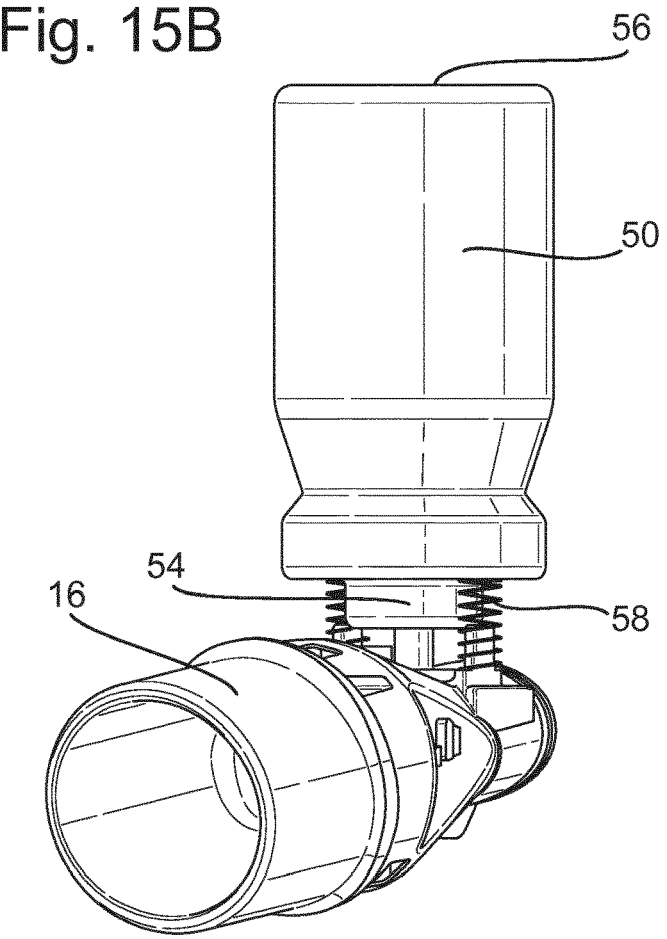

In the embodiment shown in FIG. 8, it can be seen in FIG. 8D when compared with FIG. 8C that the canister 50 moves upwardly (i.e. in the distal direction) relative to the yoke 22 and closes the spacing between the canister base 56 and the yoke collar 24. This upward movement is driven by the return spring of the canister 50, which has at least sufficient force to drive the valve stem 53 out of the canister 50 and to its rest position. In embodiments where the return spring of the canister 50 is not sufficient to reliably provide the entire upward force, one or more supplementary return springs may be provided, for example on the mouthpiece 16 to push upwardly on the canister 50 adjacent the valve 54 (as shown in FIG. 15). The canister 50 moves in the distal direction until it abuts against the yoke 22, which prevents further movement of the canister 50. As the canister base 56 is in contact with the rod 120 in the fired position of FIG. 8C, the distal movement of the canister 50 pushes the rod 120 axially back up the shaft 114 of the rotary damper 100. However the axial movement of the rod 120 is controlled since the cam follower tooth 132 must slide in the cam track 124, 126 and to do so, the rod 120 must rotate, at least for movement of the cam follower tooth 132 along the upper portion 126 of the cam track, since this upper portion 126 is generally helical in shape. The upper portion 126 may have a constant radius of curvature, but in this embodiment, the helix has two main portions, a lower one with an angle of about 25° and an upper one with an angle of about 60° (as shown in FIG. 6B). Other transitional and/or intermediate portions are also envisaged.

Rotation of the rod 120 is controlled by the rotary damper 100 and the shaft 114 rotates at a controlled speed, due to the torque of the damper 100 that must be overcome to rotate the shaft 114 of the damper 100, allowing the rod 120 to move axially along the shaft 114 in the distal direction also at a controlled speed. However once the cam follower tooth 132 reaches the beginning of the lower portion 124 of the cam track, no further rotation of the rod 120 is required to enable the distal, axial rod 120 movement, since the cam track at its lower portion 124 is linear. Thus axial movement of the rod 120 in the distal direction is much quicker in this second segment of the predetermined time period of operation of the inhaler 10 (compared with the first time segment when the cam follower tooth 132 is travelling along the helical portion 126 of the cam track). In effect, the rod 120 bypasses the control of the rotary damper 100 once it reaches the beginning of the lower portion 124 of the cam track. Therefore, as seen in FIG. 8D, the inhaler 10 resets the canister 50 and canister valve 54 irrespective of the actions of the user of the inhaler 10. Namely resetting of the inhaler 10 in this regard is automatic.

Figure 8E:
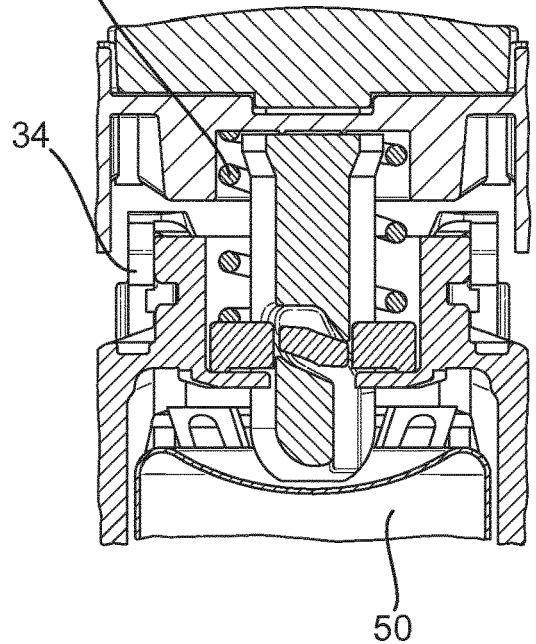

As shown in FIG. 8E, the final stage of operation of this embodiment of the invention is for the drive mechanism of the inhaler 10 to be reset so that the main spring 20 is reloaded ready to dispense a subsequent dose that is now metered into the valve 54 of the canister 50. As discussed above, proximal movement of the yoke 22 under the force of the main spring 20 is halted by the yoke feet 23 contacting the bearing surfaces 15 of the cap 14. Therefore to move the yoke 22 back to its first position, the user simply rotates the cap 14 back to the closed position (in which the cap 14 covers the mouthpiece 16, as shown in FIG. 5A). This rotates the bearing surfaces 15 and pushes upwardly on the yoke feet 23, pushing the yoke collar 24 in the distal direction and compressing the main spring 20. If the inhaler 10 has a counting mechanism 40 (see FIG. 5), distal movement of the yoke 22 in this step of operation activates the counting mechanism 40 to count the dispensed dose of medicament. The yoke plate 130 moves with the yoke 22 and so the cam follower tooth 132 moves upwards in the lower portion 124 of the cam track then along the upper portion 126 of the cam track, rotating and lifting the rod 120 back to its initial positon, in which it no longer touches the canister base 56. Rotation of the rod 120 in the resetting direction does not need to be controlled by the rotary damper 100 and is in the opposite direction to the controlled rotation. In some embodiments (not shown), it is envisaged that a damper with a clutch in the return direction could be used, resulting in a 'zero' torque return rotation. This may be advantageous as a user resetting the inhaler would not feel the reset of the damper (e.g. during cap closure) and there would not be the same peak of stress in the damper during resetting.

An alternative embodiment of the present invention is shown in FIGS. 12 to 16. Where components of the inhalers of the various embodiments are the same, the same reference numerals will be used. As discussed above, many of the components and functions of the different embodiments of the present invention are common and interchangeable and are within the scope of any of the embodiments.

An alternative embodiment of the present invention is shown in FIG. 9. This embodiment is similar to the previous embodiment illustrated in FIG. 8, and the same reference numerals will be used as appropriate. However, in this embodiment, the configuration and operation of certain components differs, as follows.

Figure 9A:
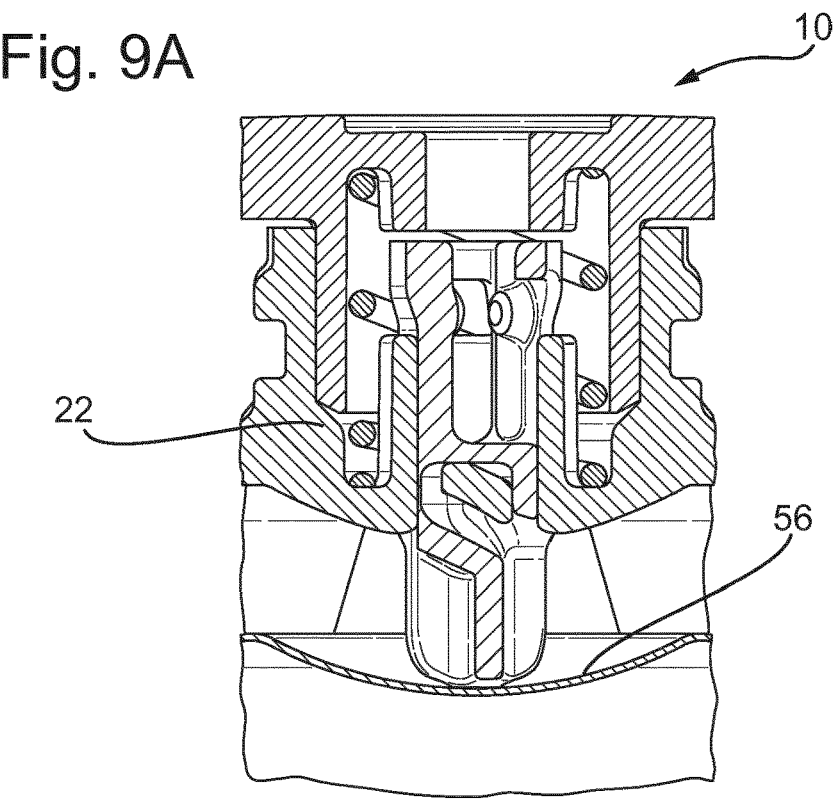
FIGS. 9A to 9F illustrate operation of another embodiment of an inhaler and damping system according to FIGS. 1 to 7, FIGS. 9G to 9I depict the rod of this embodiment from the side, the front and in perspective, respectively.
Figure 9B:
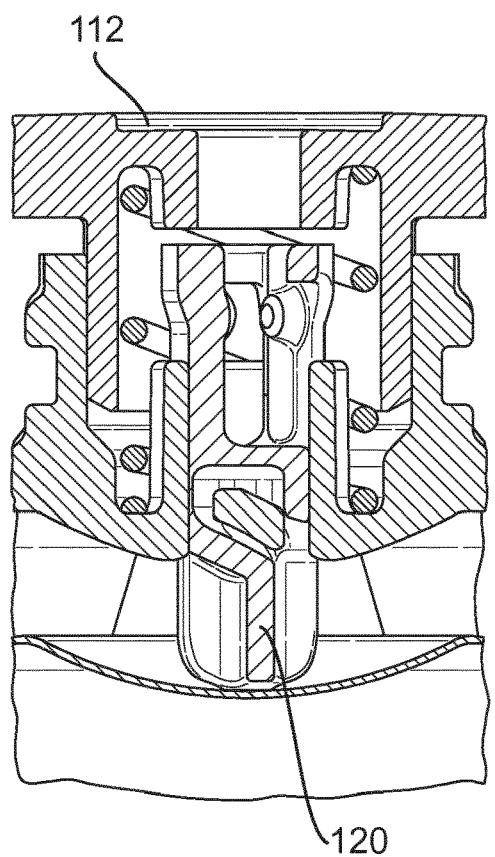
Figure 9C:
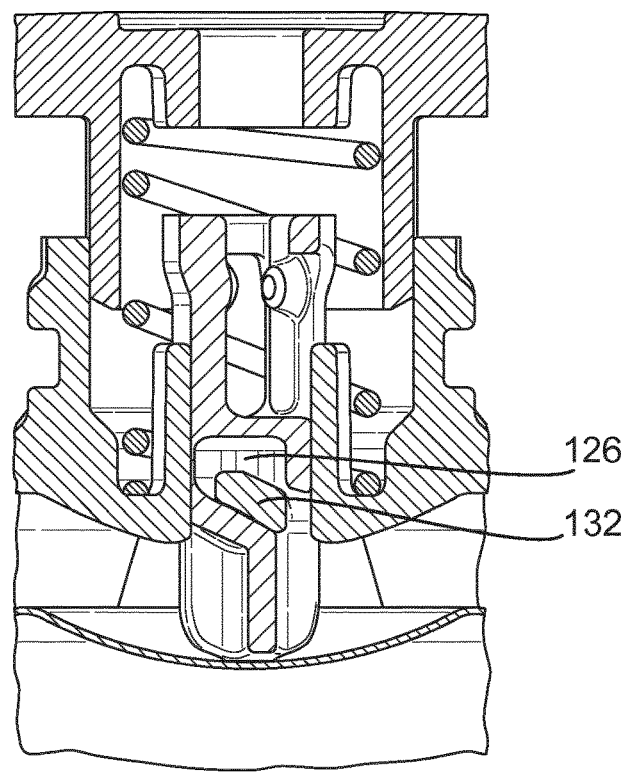
Figure 9D:
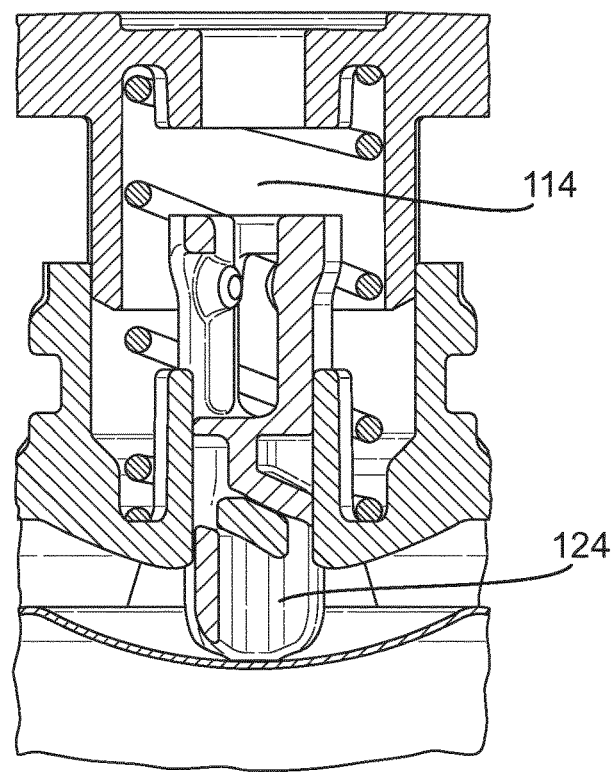
Figure 9E:
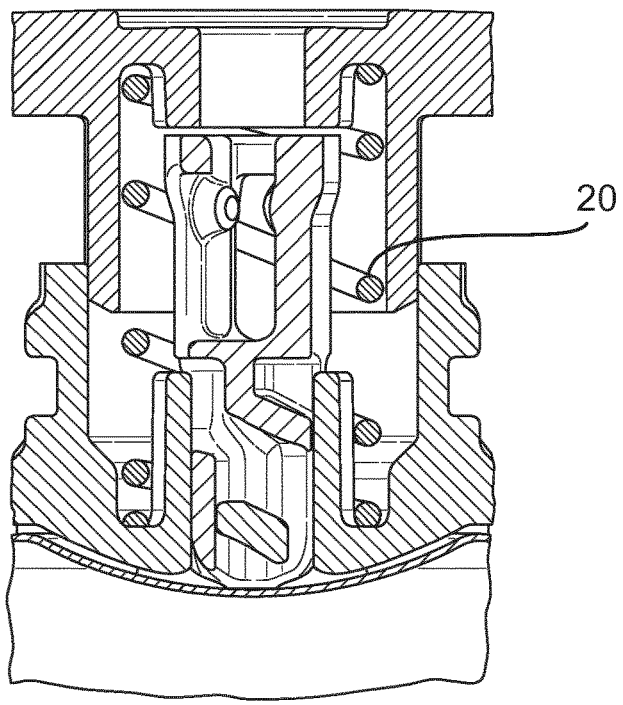

FIGS. 9A to 9F illustrate operation of this embodiment in a similar manner to FIGS. 8A to 8E of the previous embodiment. In particular, FIGS. 9A to 9C illustrate the same configuration and operational steps of the inhaler 10 as FIGS. 8A to 8C, with: FIG. 9A illustrating the inhaler 10 in its rest or closed position, in which the cap 14 is closed and the load of the compressed main spring 20 is supported or relieved; FIG. 9B illustrating the inhaler 10 in the pre-fire position; and FIG. 9C illustrating the fired position of the inhaler 10. However, what cannot be appreciated from FIG. 9C is that, in this embodiment, even though the valve stem 53 is pushed to its fullest extent into the canister 50 (and thus the canister 50 and valve stem 53 cannot be compressed any further towards each other), the feet 23 of the yoke have not yet hit the bearing surfaces 15 of the cap 14 and therefore movement of the yoke 22 is not stopped. This can best be appreciated from FIGS. 10A and 10B, with FIG. 10A showing the present embodiment in the FIG. 9C operational state (immediately after firing and with the valve stem 53 fully compressed with the canister 50) and FIG. 10B showing the previous embodiment in the FIG. 8C operational state (also immediately after firing).

Figure 10A:
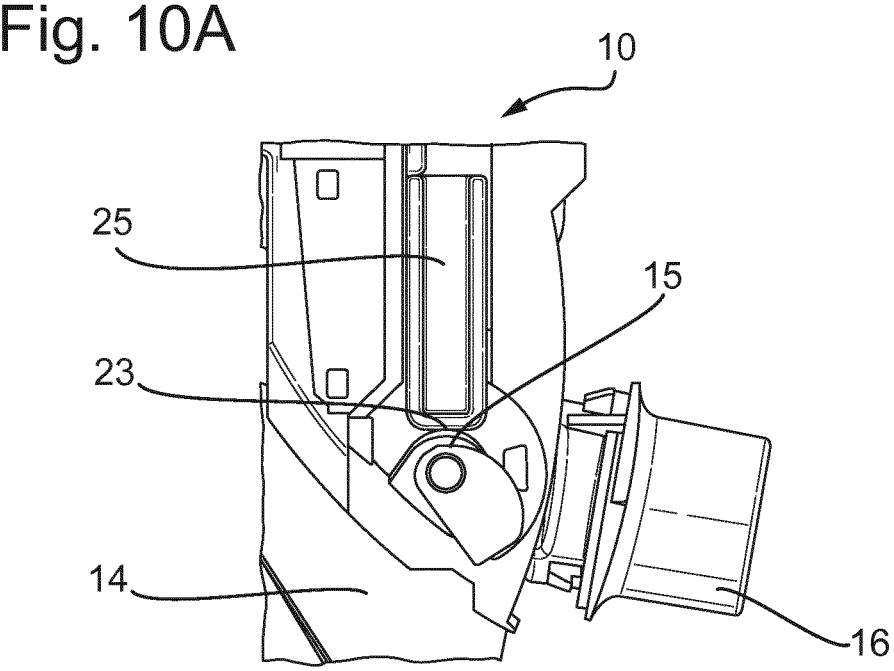
FIGS. 10A to 10D illustrate the differences between the embodiment of FIGS. 8A to 8E and the embodiment of FIGS. 9A to 9F.

As shown in FIG. 10A, there is a gap between the yoke foot 23 and the bearing surface 15 and the yoke 22 continues moving towards the bearing surfaces 15 under the load of the spring 20 until the yoke feet 23 hits the bearing surfaces 15. During this additional yoke movement, the yoke collar 24 continues to be driven towards the canister base 56 and the force from the rod 120 on the canister base 56 maintains the canister valve stem 53 in its fully fired or open configuration. As in the previous embodiment, after the inhaler 10 has been fired, the damping system 100 is configured to release the downward force of the rod 120 on the base 56 of the canister 50 in a controlled manner so as to reset the canister 50 (moving it from the actuating position in FIG. 9C to the rest position of FIG. 9E, i.e. moving the canister base 56 towards the yoke collar 24) and moving the canister valve stem 53 to its closed position. However the relative movement of the canister 50, canister valve stem 53 and yoke 22 in this embodiment is different to that of the previous embodiment in FIG. 8. As illustrated in FIGS. 9D and 9E, in this embodiment there is no upward movement of the canister 50 immediately after firing, because the return spring of the canister 50 has much less force than the drive spring 20 that continues to drive the yoke 22 downwardly. Therefore initially the rotation of the rod 120 (which is controlled by the rotary damper 100 due to the torque of the damper 100 that must be overcome), still controls the relative movement of the canister base 56 towards the yoke collar 24, but in this case the relative movement is due to the continued downward travel of the yoke 22, not due to the canister spring pushing the canister 50 upwardly. Thus, until the yoke feet 23 finally hit the bearing surfaces 15, the canister valve stem 53 is maintained in its fully compressed position in the canister 50. It can be seen in these figures that in this embodiment, the surface of the yoke collar 24 facing the canister base 56 is curved, i.e. convex, and the shape complements the shape of the canister base 56, which is concave.

Referring to FIG. 9E, it can be seen that at about the same time as the yoke feet 23 hit the bearing surfaces 15, the cam follower tooth 132 reaches the beginning of the lower portion 124 of the cam track (as the rod rotates 120) and, as with the previous embodiment, no further rotation of the rod 120 is required to enable the distal, axial rod 120 movement, since the cam track at its lower portion 124 is linear. Thus axial movement of the rod 120 in the distal direction is rapid at this stage as, in effect, the rod 120 bypasses the control of the rotary damper 100 once it reaches the beginning of the lower portion 124 of the cam track. It is at this stage in this embodiment that the compression between the canister 50 and the canister valve stem 53 is reduced and the return spring of the valve 54 (and/or any more supplementary return springs of the inhaler 10 drive the valve stem 53 out of the canister 50 and to its rest position. Whilst these operations are described as concurrent, it is possible that the cam follower tooth 132 in some embodiments reaches the beginning of the lower portion 124 of the cam track before the yoke feet 23 hit the bearing surfaces 15, as discussed below in relation to FIG. 10C.

Figure 9F:
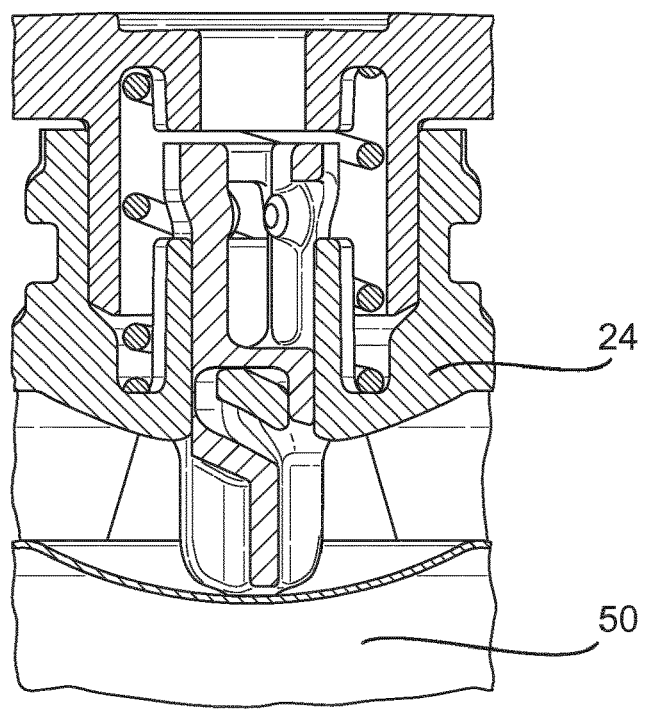
Figure 9G:
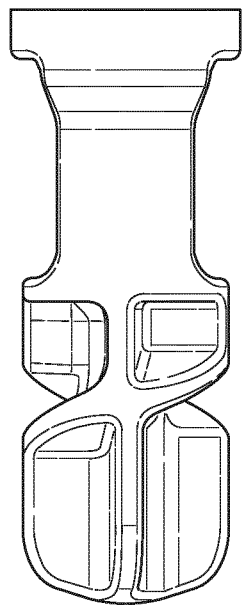
Figure 9H:
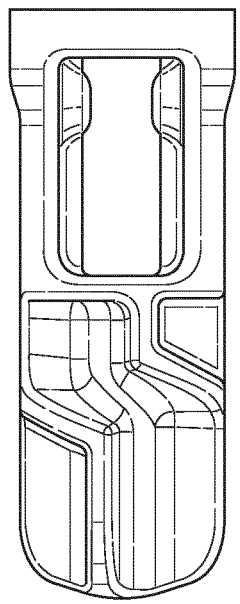
Figure 9I:
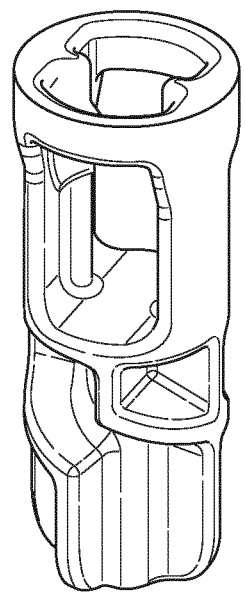
Figure 10B:
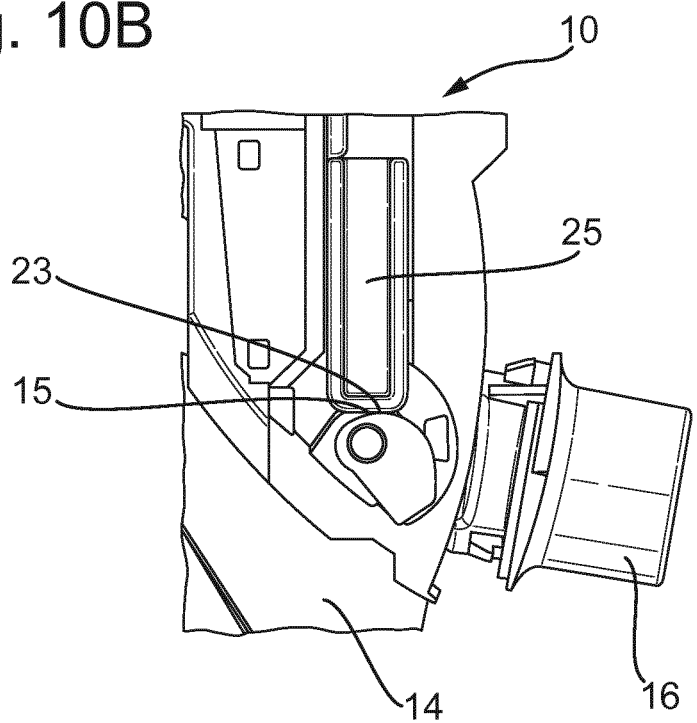

As shown in FIG. 9F, which is similar to FIG. 8E of the previous embodiment, the final stage of operation of the inhaler is for the drive mechanism to be reset so that the main spring 20 is reloaded ready to dispense a subsequent dose that is now metered into the valve 54 of the canister 50. As previously, proximal movement of the yoke 22 under the force of the main spring 20 is halted by the yoke feet 23 contacting the bearing surfaces 15 of the cap 14 and the user simply rotates the cap 14 back to the closed position, which rotates the bearing surfaces 15 and pushes upwardly on the yoke feet 23, pushing the yoke collar 24 in the distal direction and compressing the main spring 20. The yoke plate 130 moves with the yoke 22 and so the cam follower tooth 132 moves upwards in the lower portion 124 of the cam track then along the upper portion 126 of the cam track, rotating and lifting the rod 120 back to its initial positon, in which it no longer touches the canister base 56. This final stage of operation is the same as for the previous embodiment.

Figure 10C:
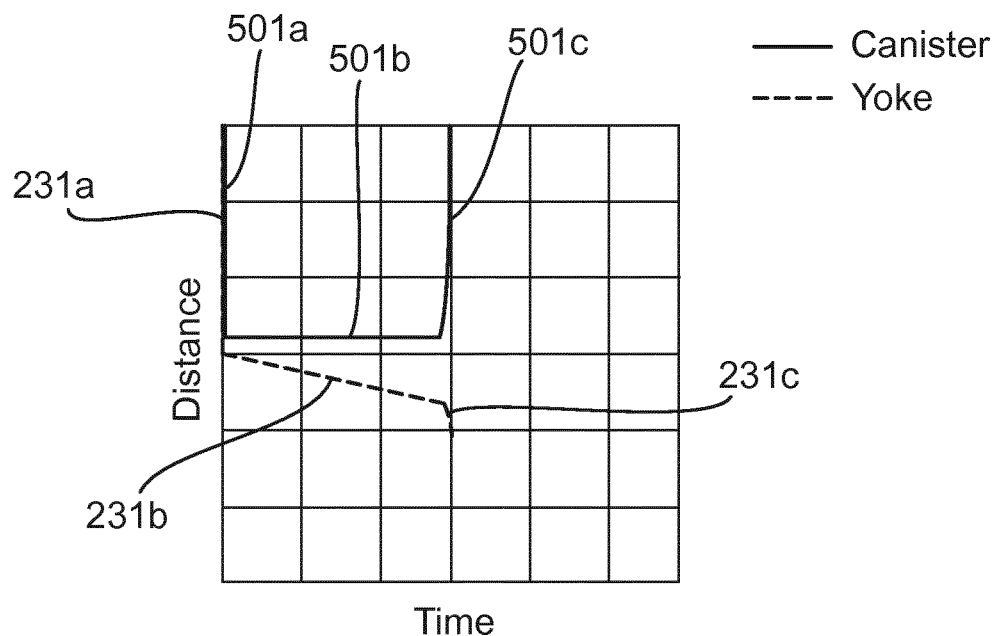

The difference in operation between the two embodiments is illustrated in FIG. 10, with FIG. 10C illustrating operation, and in particular, movement of two of the components of the FIG. 9 inhaler 10. FIG. 10D illustrates movement of the same components during operation of the inhaler 10 of FIG. 8 (and for reference FIG. 19 also illustrates movement of one of these components of this embodiment and is discussed further below). Referring to FIGS. 10A and 10C, and as described above, on firing the inhaler 10 of the embodiment illustrated in FIG. 9, the canister valve stem 53 is compressed into the canister as the yoke 22 travels downwardly, and the maximum compression of the valve stem 53 into the canister is reached before the feet 23 of the legs 25 of the yoke 22 hit the bearing surfaces 15 of the cap. Downward movement of the canister 50 as the valve stem 53 is compressed into the canister valve 54 is illustrated by line 501a of FIG. 10C, with distance being on the y-axis. This is the same for the FIG. 8 embodiment, as illustrated by line 502a of FIG. 10D. Initial downward movement of the yoke 22 is illustrated by line 231a of FIG. 10C. As maximum compression of the valve stem 53 into the canister 50 is reached, the canister 50 is held in the compressed state (i.e. with the valve 54 fully open) for a period on time as indicated along the x-axis. Namely the canister 50 does not move upward or downward, as indicated by line 501b. Meanwhile the yoke 22 continues to move downwardly as the feet 23 have not yet come into abutment with the bearing surfaces 15. Both lines 231a and 501a are almost vertical, indicating the rapid motion of these components under the force of the spring 20 initially. However continued movement of the yoke 22 once the canister 50 is fully compressed is controlled by the damping mechanism 100 as discussed above, hence the movement is slower, as indicated by the sloped line 231b of FIG. 10C.

As the rod 120 rotates under control of the damping mechanism 100, the cam follower tooth 132 moves along the upper cam track 126 until it reaches the junction with the lower cam track 124. At this point, the rod 120 is released and can move rapidly in the axial direction, allowing the valve stem 53 to be released from the canister 50 and thus moving the canister upwards rapidly, as illustrated by line 501c. In this embodiment, the yoke feet 23 are still not quite in contact with the bearing surfaces 15 and so the yoke 22 moves rapidly downwards to its rest point, as illustrated by line 231c. The force of the return springs is not as great as the force of the drive spring 20, so the lines 501c and 231c are not as close to vertical as lines 501a and 231a.

Figure 10D:
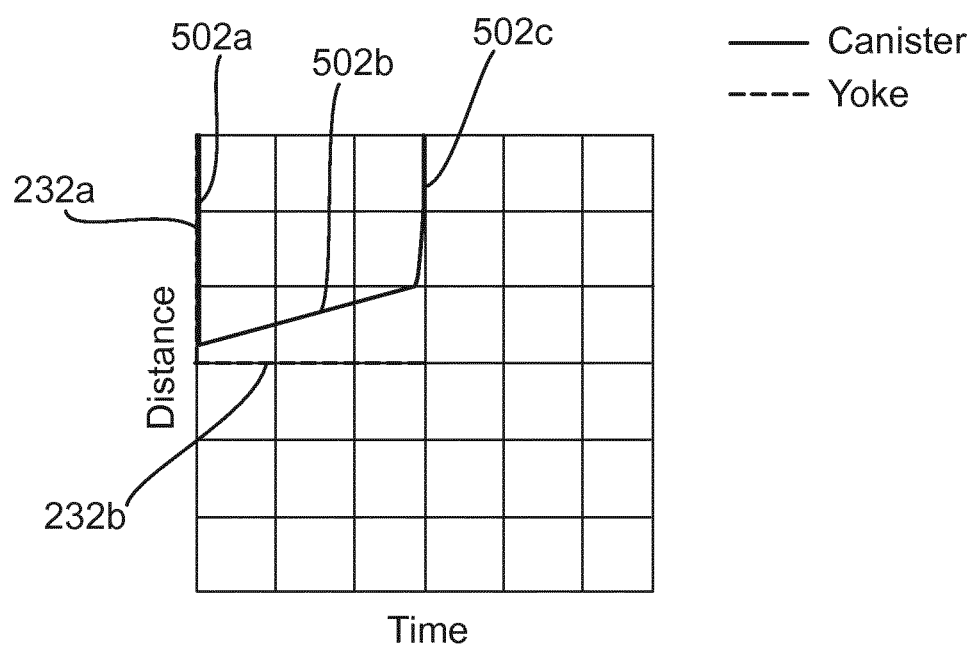
Figure 11A:
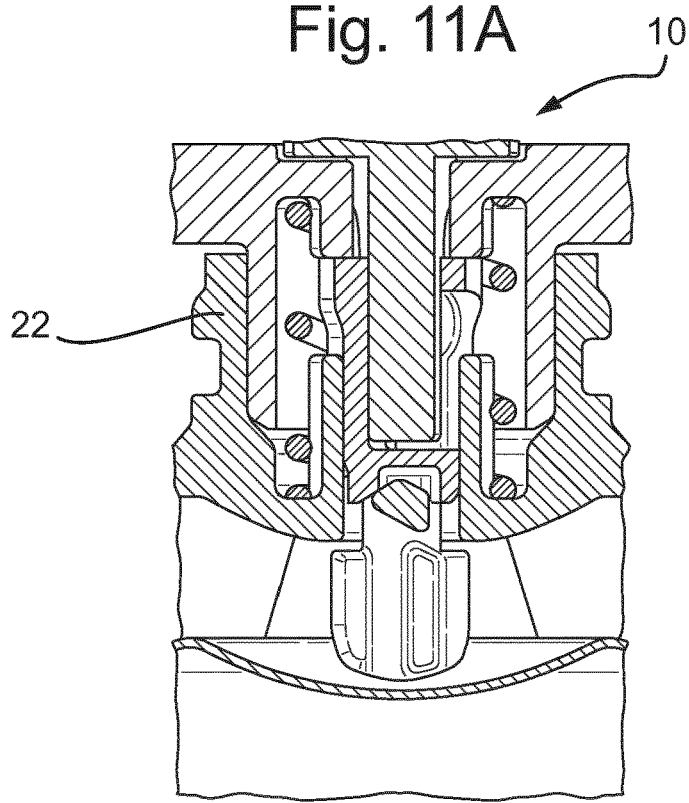
FIGS. 11A to 11F illustrate operation of another embodiment of an inhaler and damping system according to FIGS. 1 to 7, FIGS. 11G to 11I depict the rod of this embodiment from the side, the front and in perspective, respectively.
Figure 11B:
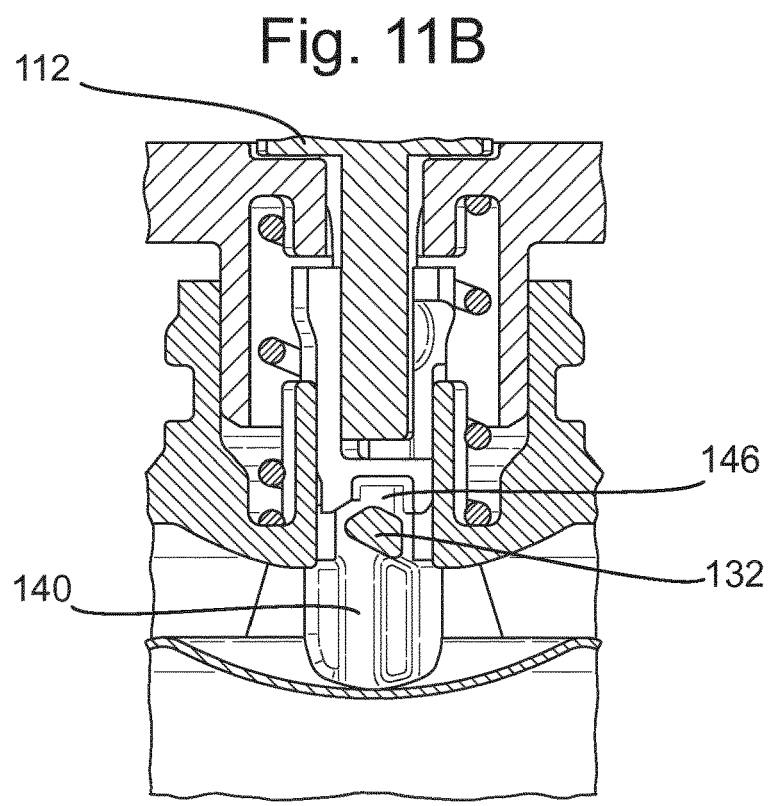
Figure 11C:
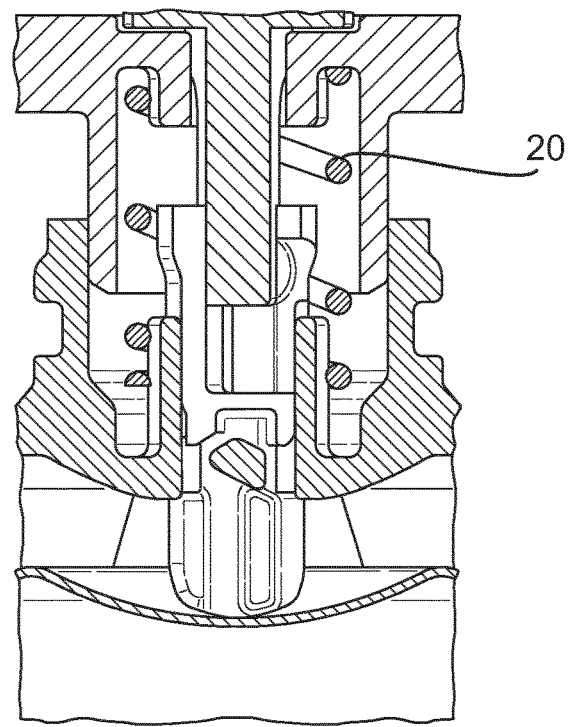
Figure 11D:
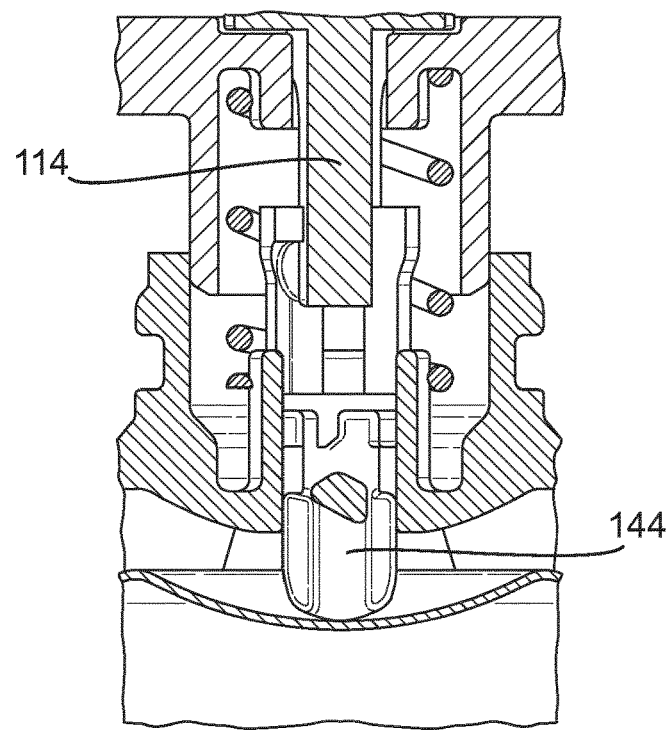
Figure 11E:
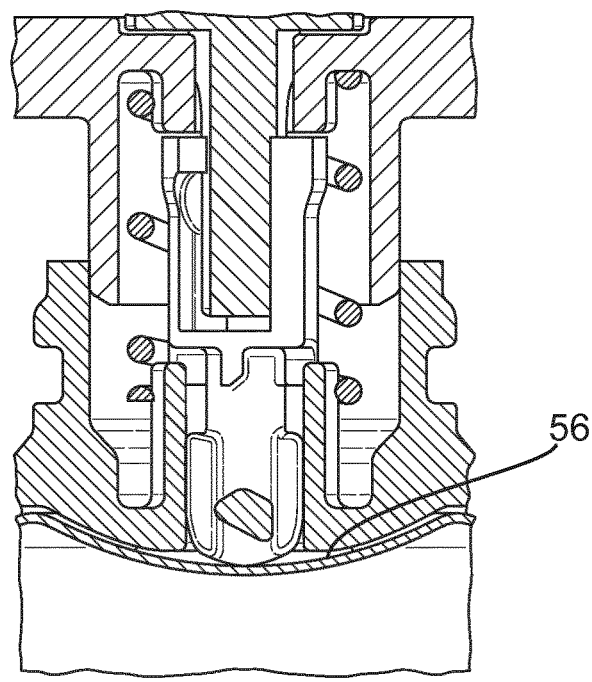
Figure 11F:
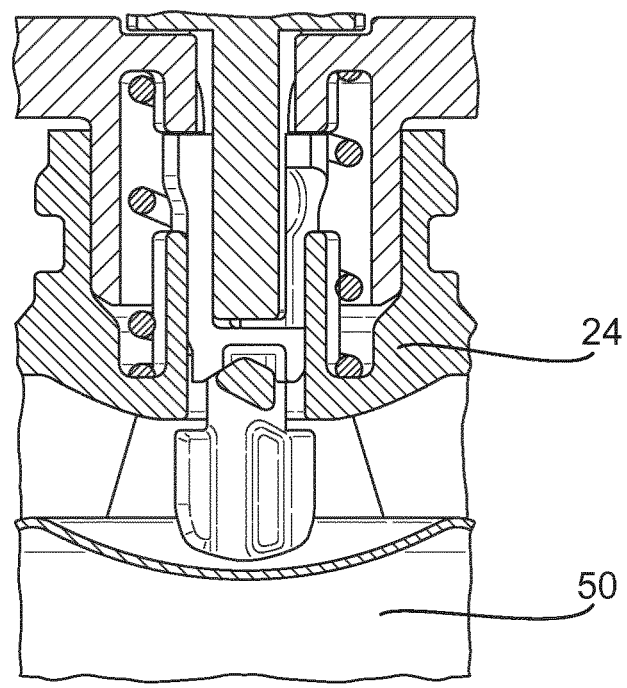
Figure 11G:
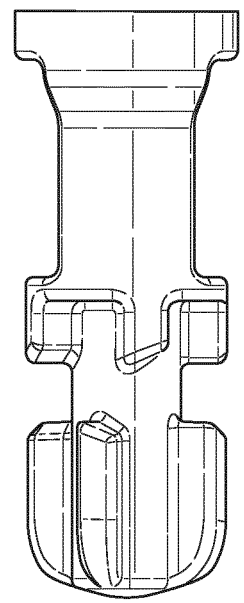
Figure 11H:
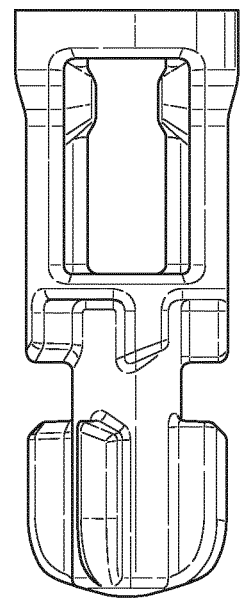
Figure 11I:
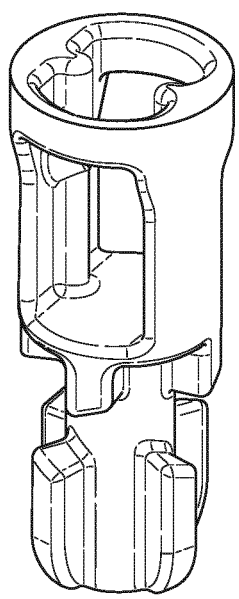

In contrast, in the embodiment illustrated in FIG. 8 and referring to FIG. 10D, it can be seen that the yoke 22 moves rapidly under the force of the driving spring 20 and then stops once the yoke feet 23 abut the bearing surfaces 15, as shown by lines 232a and 232b respectively. Thus movement of the yoke 22 is not controlled by the damping mechanism 100. Rather it is movement of the canister 50 that is controlled by the damping mechanism 100, at a first, slower speed, as illustrated by line 502b and then released more rapidly as illustrated by line 502c, when the second portion of the cam track 124 is reached by the cam follower tooth 132. The difference between these two arrangements is the length of time the canister valve 54 is maintained with the valve stem 53 fully compressed and whether release of the valve stem 53 from the compression is rapid or is more controlled before a rapid final release. Both arrangements are advantageous for dispensing metered doses of medicament.

A still further embodiment is illustrated in FIG. 11. This embodiment is similar to the embodiment of both FIGS. 8 and 9, but with a modified rod 140 in place or the rod 120 of the other embodiments. In this embodiment, the rod 140 is shaped such that it rotates in only a single direction, whether the rod 140 is moving upwards or downwards relative to the shaft 114 of the damping mechanism 100. The rod 140 has cam track portions 144 and 146 that are configured differently to the other rods 120 and enable the rod 140 to move axially in either direction whilst still rotating in only a single direction. This has the advantage of accommodating any slack that might otherwise occur when the rod changes direction.

Figure 17A:
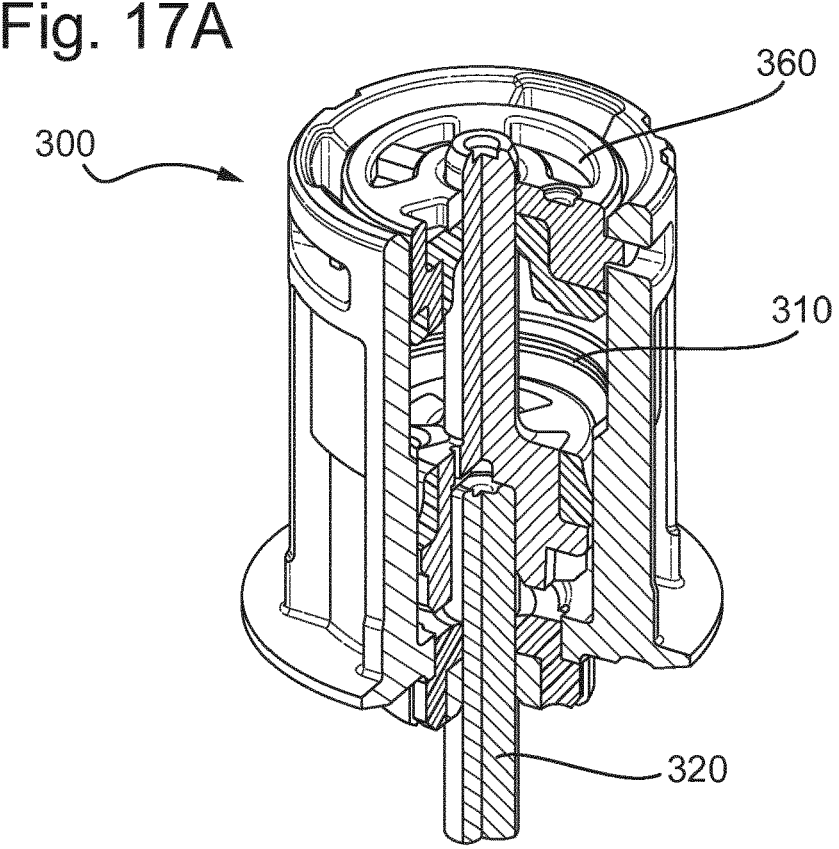
FIG. 17A is a perspective view of a damping system in accordance with another alternative embodiment of the present invention and FIG. 17B is a cut-away view of the damping system of FIG. 17A.
Figure 17B:
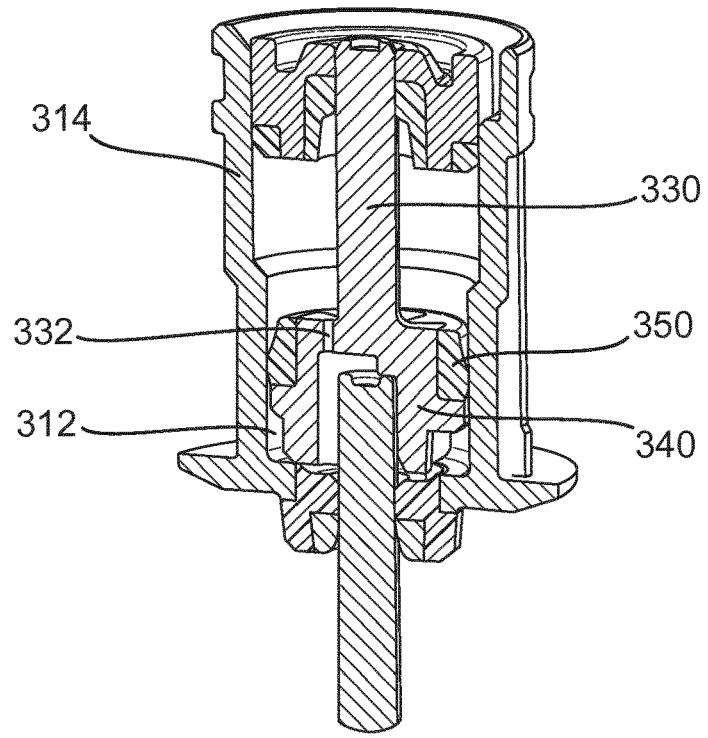
Figure 18A:
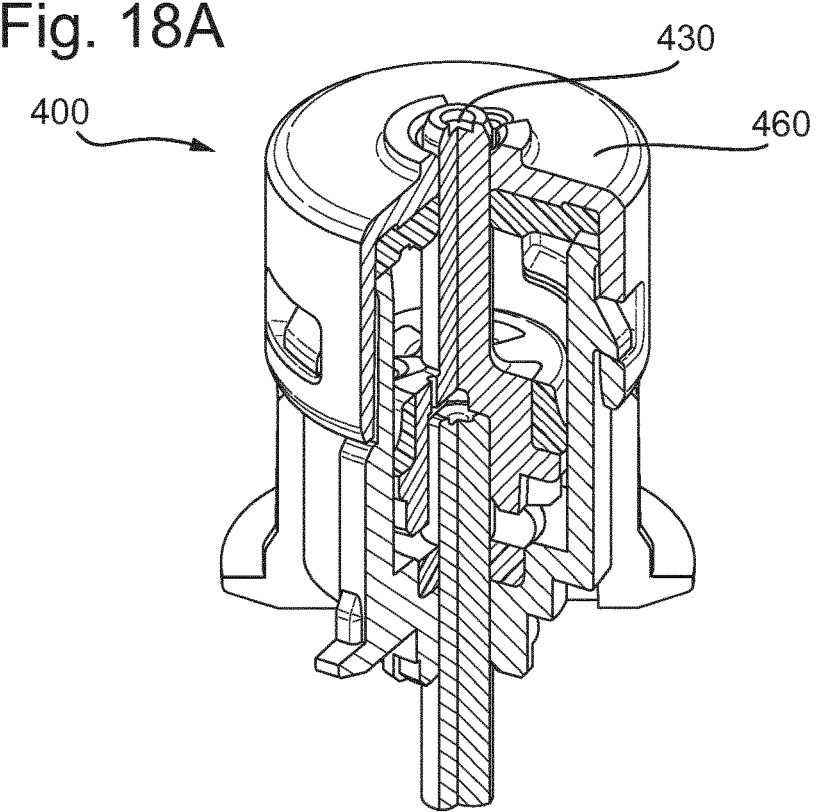
FIG. 18A is a perspective view of a damping system in accordance with another alternative embodiment of the present invention and FIG. 18B is a cut-away view of the damping system of FIG. 18A.
Figure 18B:
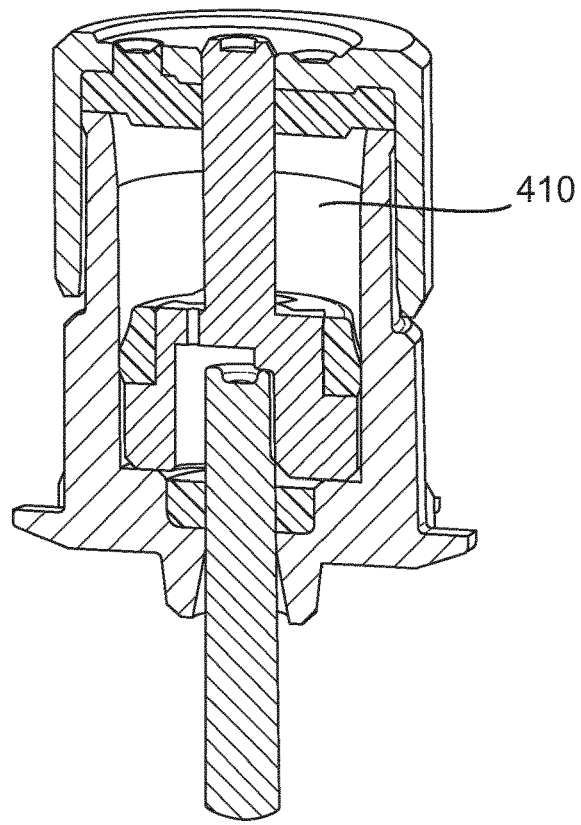

Referring to FIG. 12, an alternative damping system 200 for use in an inhaler 10 according to the present invention is illustrated. The damping system 200 functions in a similar manner to the damping system 100 of the previous embodiment, but in this embodiment the damper is a linear damper rather than a rotary damper. The linear damper 200 comprises a piston 220, which performs a similar function as the rod 120 of the rotary damper 100 embodiment. The piston 220 passes through a reservoir 210, which contains an incompressible fluid such as silicone oil. The viscosity of the silicone oil is optimised for operation of the linear damper 200 and may have a viscosity of about 250 cSt for example. The piston 220 protrudes from the upper and lower extremities of the reservoir 210, thus having a distal protruding end 228 and a proximal protruding end 227, the proximal protruding end 227 contacting the canister 50 when the inhaler 10 is in operation, as discussed further below. The piston 220 is sealed within the reservoir 210 by upper distal seals 230 and plug 235 sealing the distal protruding end 228 of the piston 220 and by a lower proximal seal 240 sealing the proximal protruding end 227. The seals 230, 240 are configured to prevent or at least minimise any egress of silicone oil (or whatever hydraulic fluid is used) from the reservoir 210, particularly as the piston 220 moves axially as discussed further below. Whilst a single piston 220 is described in this embodiment, it is possible that a pair of aligned pistons (such as shown in FIGS. 17 and 18) could alternatively perform the same functions as the piston 220 of this embodiment.

Figure 13A:
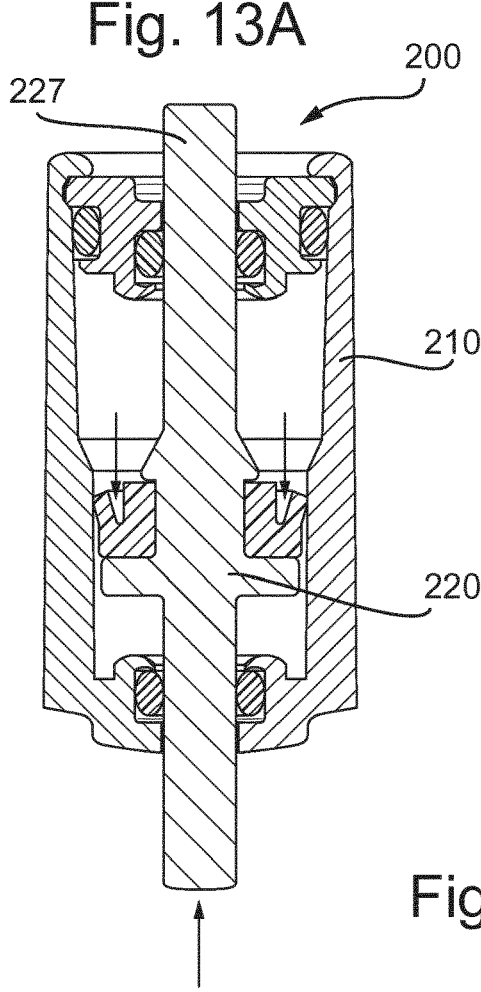
FIGS. 13A to 13C are front views of the damping system of FIG. 12 in various operational states.
Figure 13B:
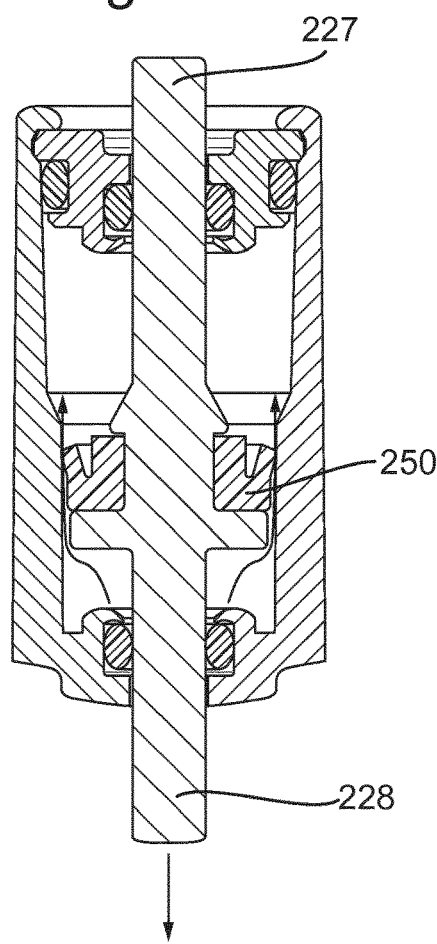
Figure 13C:
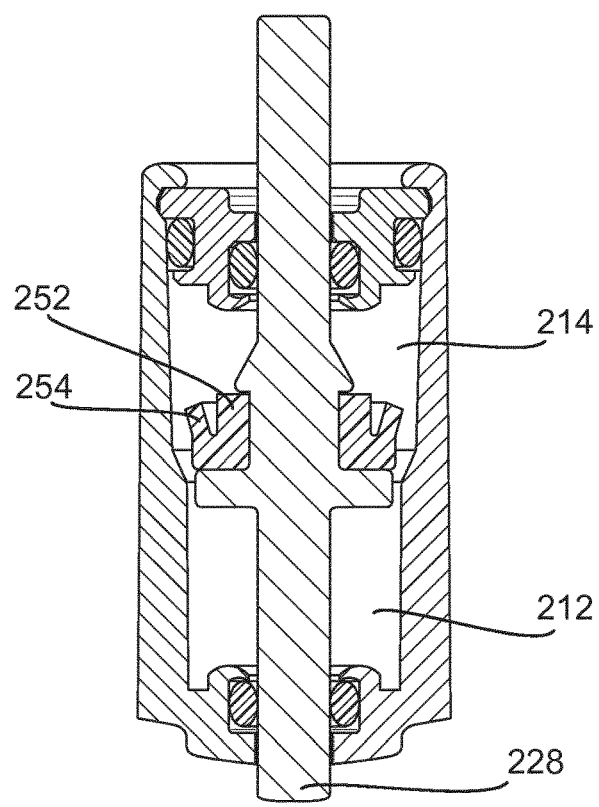
Figure 14A:
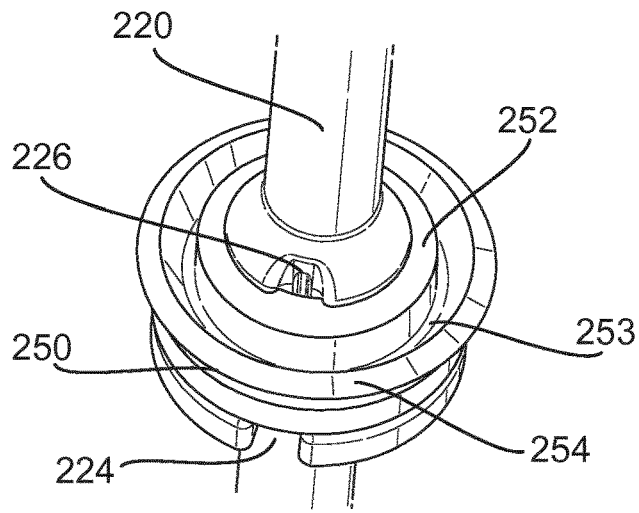
FIGS. 14A to 14C are perspective views of a lip seal and a piston of the damping system of FIGS. 12 and 13.

The reservoir 210 of the damping system 200 is generally cylindrical and has two chambers 212, 214. The upper or distal chamber 214 has an inner diameter that is larger than the inner diameter of the lower or proximal chamber 212. As shown in FIGS. 12 and 13, in this embodiment the transition between the two chambers 212, 214 is a tapered edge, though this is not essential. As is further shown in these figures, the damping system 200 further comprises a piston seal 250 (see also FIG. 14). The piston seal 250 surrounds and seals against the piston 220 and has an outer diameter such that it also seals against the inner diameter of the proximal chamber 212. The piston seal 250 thus fluidly isolates the proximal chamber 212 from the distal chamber 214 when the piston seal 250 is located in the proximal chamber 212. However the outer diameter of the piston seal 250 is smaller than the inner diameter of the distal chamber 214 so the piston seal 250 does not fluidly isolate the proximal chamber 212 from the distal chamber 214 when the piston seal 250 is located in the distal chamber 214 (as shown in FIG. 13C). Movement of the piston seal 250 is governed by the position of the piston 220, since the piston seal 250 is retained between protruding rings 223 and 225 of the piston 220 (as seen in FIG. 14A for example). The damping system 200 is configured such that the piston 220 moves axially within the reservoir 210, moving the protruding ends 227, 228 of the piston 220 towards or away from the reservoir 210 accordingly and moving the piston seal 250 between the chambers 212, 214.

Figure 14B:
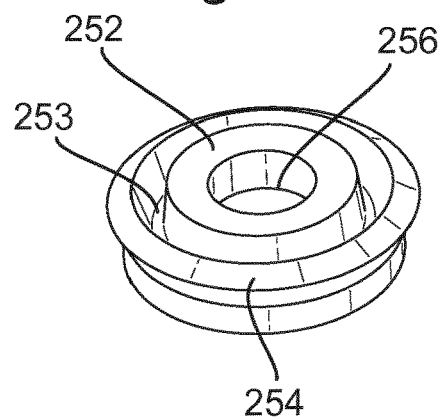
Figure 14C:
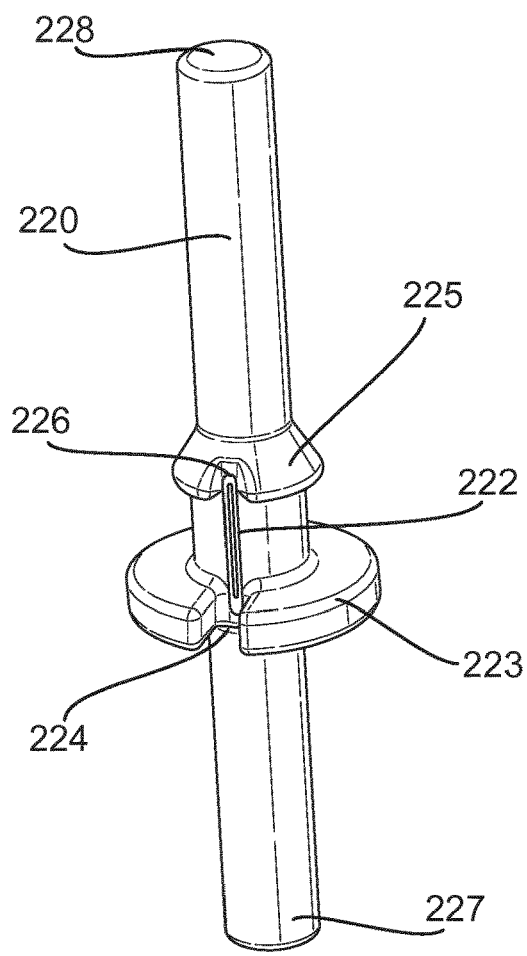

As illustrated in FIGS. 14A and 14B, the piston seal 250 comprises a lip seal having concentric upright ring portions 252, 254 spaced apart by a thinner, separating section 253, and a central bore 256 through which the piston 220 is received. Thus the piston seal 250 has a degree of radial flexibility as discussed further below. In the region of the piston 220 where the piston seal 250 is located in use, there is an axial channel 222 in an outer surface of the piston 220. The channel 222 is of a length such that it is longer than the depth of the piston seal 250 and has inlets/outlets 224, 226 at either end of the channel 222 that are open to the fluid in the reservoir 210 and, as shown in FIG. 14A, are open above and below the piston seal 250. Most of the mid-portion of the channel 220, which is an open channel cut or otherwise formed or moulded in the surface of the piston 220, is sealed by the piston seal 250.

Operation of an inhaler 10 having the linear damping system 200 of this embodiment will now be described, with reference to FIGS. 12 to 16. Much of the operation of the inhaler 10 of this embodiment is the same as operation of the inhaler 10 of the embodiment having a rotary damping system 100 and the earlier disclosure also applies to this embodiment. Referring to FIG. 16A, the inhaler 10 is illustrated in its rest or closed position, in which the cap 14 is closed and the load of the compressed main spring 20 is supported or relieved as previously discussed, by the bearing surfaces 15 of the cap 14 abutting the feet 23 of the yoke 22 and thus holding the load of the main spring 20. Again, this is the configuration (shown in FIG. 5A) in which the inhaler 10 will mostly be held as it is only when the inhaler 10 is to be used that the cap 14 will be opened. As before, other components of the inhaler 10 are relieved from any significant stresses whilst in this configuration and, in this embodiment, the piston 220 is raised above the canister 50 so it does not touch the canister base 56 and the latch mechanism 34 (partially visible in FIG. 16A and also shown in FIG. 16E) is not substantially holding the load of the spring 20.

As before, when the user wishes to inhale a dose from the inhaler 10, the first step is to open the cap 14, which rotates the bearing surfaces 15 of the cap 14 and the yoke 22 moves slightly in the proximal direction under the force of the main spring 20, as shown in FIG. 16B. Again the main spring 20 is not released in this pre-fire position because the latch 34 becomes engaged as the yoke 22 moves to this first, pre-fire position. As the linear damping system 200 is formed within (or otherwise affixed to) the yoke 22, movement of the yoke 22 also moves the piston 220 into contact with the base 56 of the canister 50. In this configuration, the inhaler 10 is ready to fire to release a dose of medicament from the canister valve 54.

Figure 16C:
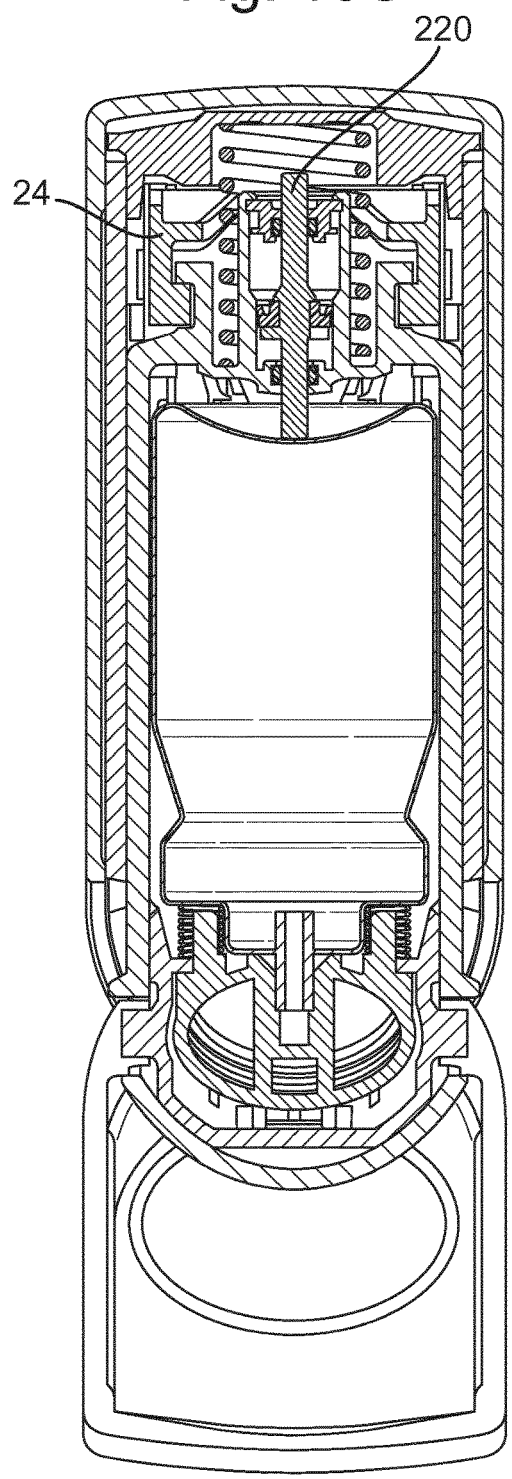

As discussed above, when the user inhales through the mouthpiece 16 the latch mechanism 34 is released and the main spring 20 unloads, pushing downwardly on the yoke 22. The force of the spring 20 is large and the yoke 22 moves rapidly to a second, fired position, which is shown in FIG. 16C. Movement of the yoke 22 is again stopped when the feet 23 of the yoke 22 hit the bearing surfaces 15 of the cap 14. The rapid movement of the yoke 22 forces the piston 220 to likewise move rapidly downward and to push on the base 56 of the canister 50, releasing a metered dose from the valve 54 into the mouthpiece 16 for inhalation by the user as before. As is shown in FIGS. 16B and 16C (also referring to FIG. 13A), the piston seal 250 throughout these stages of operation of the inhaler 10 is located in the proximal chamber 212 and fluidly isolates the proximal chamber 212 from the distal chamber 214 so that fluid cannot pass therebetween except for bleeding through the narrow channel 222 of the piston 220. The movement of the yoke 22 when firing is so rapid (just a few milliseconds) that fluid cannot flow through the channel 222 within this time, or at least not a significant or consequential amount, so the piston 220 is moved with the yoke 22 and pushes downwardly on the canister base 56 with effectively the same force that which moves the yoke 22.

As for the previous embodiment, the initial spacing between the canister base 56 and the yoke collar 24 is maintained, as shown in FIG. 16C. Thereafter, the damping system 200 is configured to release the downward force of the piston 220 on the base 56 of the canister 50 in a controlled manner so as to reset the canister 50 (moving it from the actuating position in FIG. 16C to the rest position of FIG. 16D) and moving the canister valve 54 to its closed position. Again it can be seen in FIG. 16D when compared with FIG. 16C that the canister 50 moves upwardly (i.e. in the distal direction) and closes the spacing between the canister base 56 and the yoke collar 24, until the canister 50 contacts the yoke 22. Again this upward movement is driven by the return spring of the canister 50, which has at least sufficient force to drive the valve stem 53 out of the canister 50 and to its rest position. However with this arrangement it may be that the canister spring requires assistance to drive the valve stem 53 to its rest position within a desired time period. Therefore, as shown in FIG. 15, one or more supplementary return springs 58 may be provided, for example on return spring protrusions 59 of the mouthpiece 16, to push upwardly on the canister 50 adjacent the valve 54. As mentioned previously, the canister 50 moves in the distal direction until it abuts against the yoke 22, which prevents further movement of the canister 50. As the canister base 56 is in contact with the piston 220 in the fired position of FIG. 16C, the distal movement of the canister 50 pushes the piston 220 axially through the reservoir 210. However the axial movement of the piston 220 is controlled since fluid must pass from the distal chamber 214 to the proximal chamber 212 to allow the piston 220 to move in the distal direction, but this can only occur through the channel 222 whilst the piston seal 250 seals against the inner wall of the proximal chamber 212. The channel 222 is relatively narrow and restricts fluid flow so the movement of the piston 220 is relatively slow and controlled initially. As illustrated in FIG. 13A, downward pressure from the fluid in the distal chamber 214, particularly between the rings 252, 254 of the piston seal 250, resists movement of the piston 220.

Figure 16D:
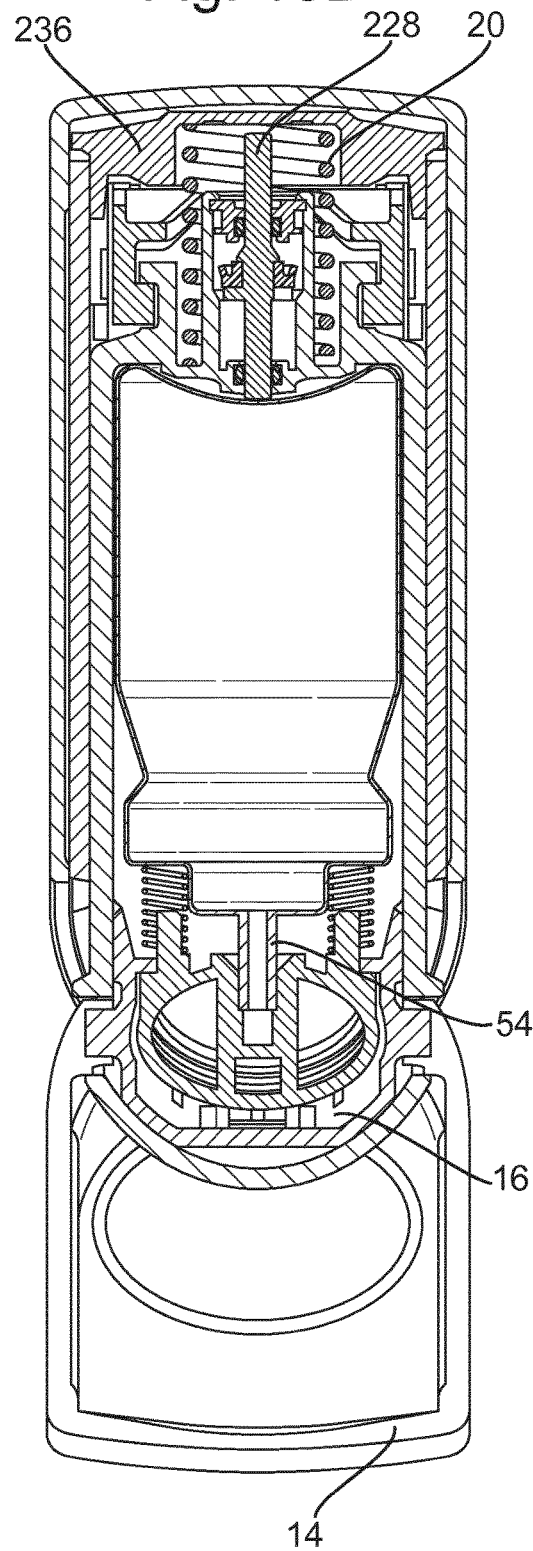
Figure 16E:
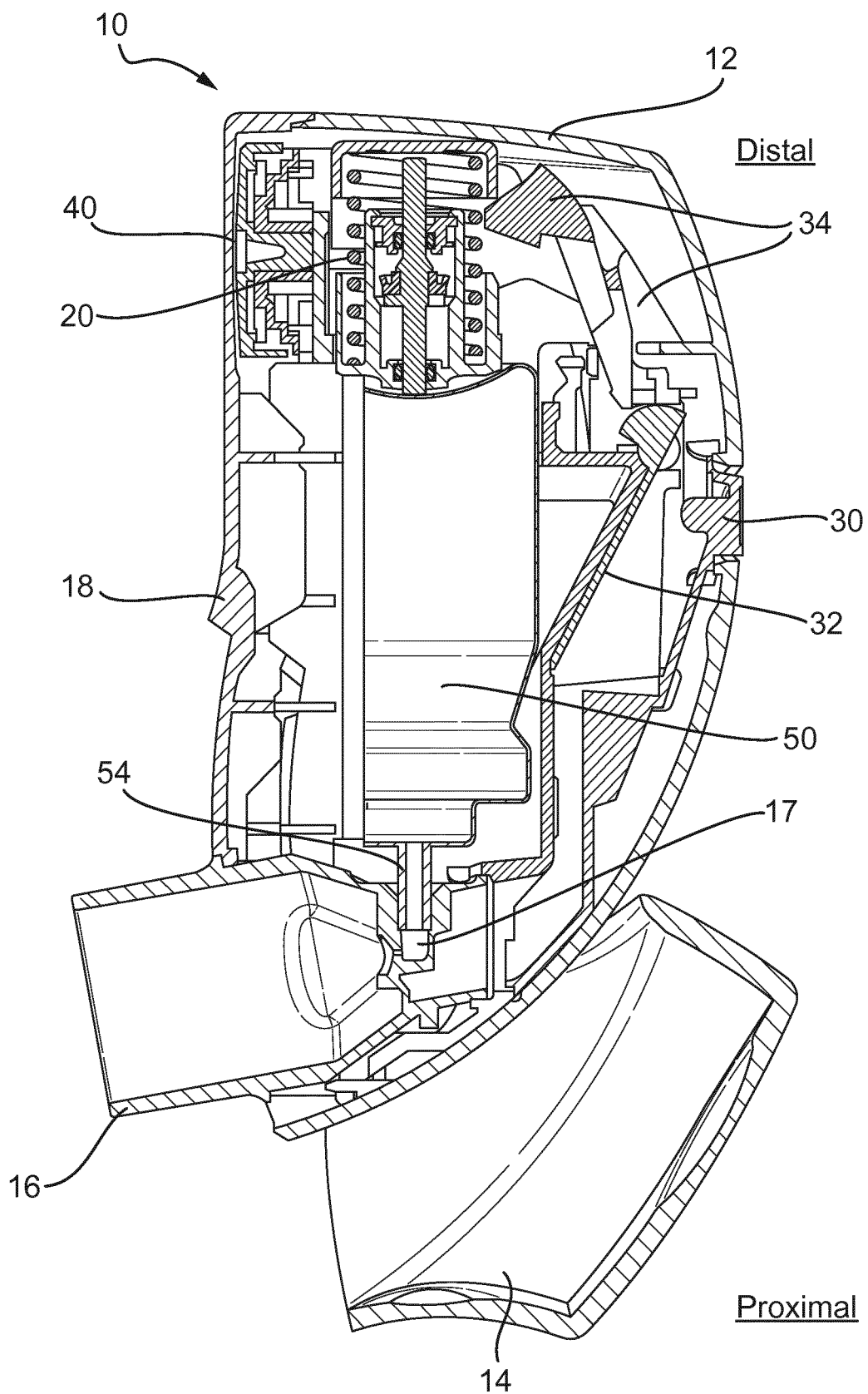

However once the piston seal 250 reaches the taper between the two chambers 212, 214, the seal against the inner surface of the reservoir 210 starts to leak and fluid passes around the outside of the piston seal 250. Soon after the piston seal 250 passes into the distal chamber 214 and no longer contacts the inner surface of the reservoir 210 due to the larger diameter of the distal chamber 214. Fluid is now able to flow quite freely between the chambers 212, 214 and the piston 220 moves axially in the distal direction much more quickly in this second segment of the predetermined time period of operation of the inhaler 10 (compared with the first time segment when piston seal 250 sealed against the inner surface of the proximal chamber 212). In effect, the piston 220 reaches a fluid bypass once the piston seal 250 leaves the proximal chamber 212 and enters the distal chamber 214 and little if any damping occurs at this stage and furthermore, as the piston seal 250 is not in contact with the chamber wall, there is no piston seal friction to resist movement either. Therefore, as seen in FIGS. 16D and 16E (the latter of which is a side view of the inhaler 10 of FIG. 16D), the inhaler 10 resets the canister 50 and canister valve 54 irrespective of the actions of the user of the inhaler 10. Resetting of the inhaler 10 in this regard is again automatic.

The final stage of operation of this embodiment of the invention is again for the drive mechanism of the inhaler 10 to be reset so that the main spring 20 is reloaded ready to dispense a subsequent dose that is now metered into the valve 54 of the canister 50. As discussed above, proximal movement of the yoke 22 under the force of the main spring 20 is halted by the yoke feet 23 contacting the bearing surfaces 15 of the cap 14. Therefore to move the yoke 22 back to its first position, the user simply rotates the cap 14 back to the closed position (in which the cap 14 covers the mouthpiece 16, as shown in FIG. 16A). This rotates the bearing surfaces 15 and pushes upwardly on the yoke feet 23, pushing the yoke collar 24 in the distal direction and compressing the main spring 20. Movement of the piston 220 in the distal direction, however, is restricted by the main spring cover 236 in the top section of the inhaler body 12, as the distal protruding end 228 of the piston 220, which piston 220 has already been moved axially in the distal direction by the canister 50 as previously discussed, now comes into abutment with the main spring cover 236, having moved only a short distance (sufficient to move the piston 220 out of contact with the canister base 56). Thus the piston 220 cannot move any further as the yoke 22 is raised to its most distal position and instead the reservoir 210 is raised and the piston 220 therefore moves proximally relative to the reservoir 210, thus returning the piston seal 250 to the proximal chamber 212, ready for the next actuation, as illustrated in FIG. 16A. An advantage of these embodiments is that pressure relief occurs during device reset. The seal 250 effectively collapses during closure of the cap 14, leading to no pressure build up in the damper 200 during a high stress event.

Further alternative embodiments of the present invention are shown in FIGS. 17 and 18. These figures show two further linear dampers 300, 400 that operate in a similar manner to the previous embodiment but have different configurations in some aspects. The linear dampers 300, 400 operate the inhalers 10 of the present invention in the same manner as discussed above in relation to the first linear damping system 200.

FIG. 17 illustrates a linear damper 300 with a reservoir 310 having a piston part 320 that protrudes from a proximal end of the reservoir 310. The proximal part of the piston 320 is axially moveable relative to the reservoir 310 to push the canister 50 of the inhaler as described in relation to the previous embodiment. The damping system 300 of this embodiment comprises a second piston part 330 that protrudes from a distal end of the reservoir 310. The distal piston part 330 has a sealing portion 340 that seals against the inside of the reservoir 310 (with the assistance of a seal 350). The sealing portion 340 fluidly isolates a proximal chamber 312 of the reservoir 310 from a distal chamber 314 of the reservoir 310 and a bleed hole 332 of the sealing portion 340 allows controlled flow of fluid therebetween to control movement of the piston parts 320, 330 axially in the proximal and distal directions, similar to as described previously. In the FIG. 17 embodiment, the distal piston part 330 is sealed within the reservoir 310 with a bayonet fitting 360 in the housing of the reservoir 310. FIG. 18 illustrates a very similar, alternative embodiment in which the damping system 400 seals a distal piston part 430 within a reservoir 410 with a clip arrangement 460 in the housing of the reservoir 410 over a distal portion of the damping system 400.

Figure 20:
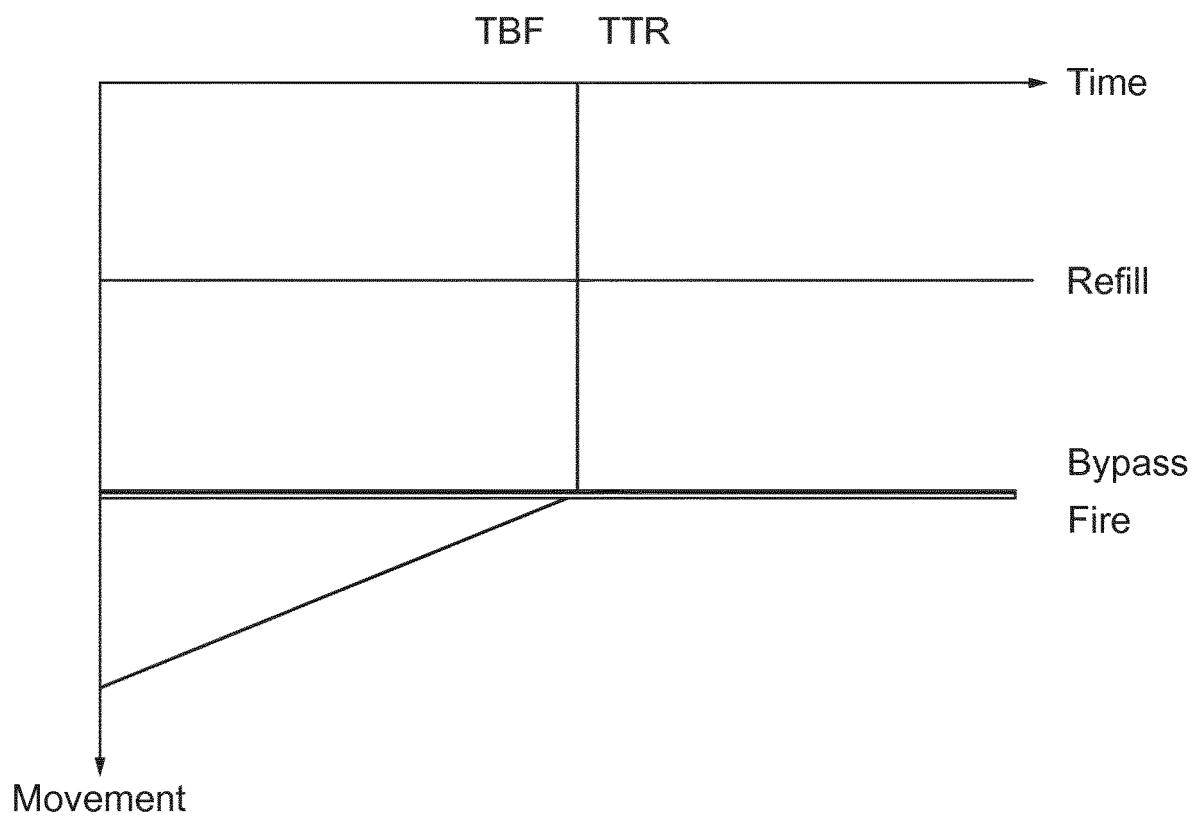
FIG. 20 is a plot indicating the ideal operation of inhalers according to embodiments of the present invention.

As discussed above, embodiments of the present invention advantageously provide inhalers 10 which automatically reset after dispensing a dose irrespective of user interaction with the inhalers 10. This is important because effective and reliable dosing from such inhalers 10 is an important requirement of these devices and variation between doses in terms of the amount of medication provided to the user is undesirable. The inhalers 10 of the embodiments of the present invention are very effective in this regard. For example, with reference to FIG. 19, performance of a rotary damper embodiment is shown. The x-axis of the plot illustrates time, where the zero time is immediately at the time of releasing the main spring 20 to fire a dose from the inhaler 10. The y-axis of the plot illustrates movement of the canister 50 (measured as displacement of the canister 50 from its rest position). When the main spring 20 is released at point 68 to move the yoke 22 to dispense a dose as described in relation to the embodiments above, the canister 50 is rapidly displaced to point 70 to its maximum displacement to actuate the valve 54. As can be seen in FIG. 19, this displacement is almost instantaneous, taking only a few milliseconds. As the valve stem 53 is compressed into the canister 50 by this displacement, the valve stem 53 reaches (and indeed moves beyond) its fire point. To ensure the full dose is dispensed, the valve 54 should be held open at or beyond the fire point for a sufficient period (known as Time Below Fire, TBF 60). At the very minimum the TBF should be greater than 275 ms in this embodiment, which is illustrated by line 80. The embodiment shown in FIG. 19 more than exceeds this minimum time period, holding the valve 54 open until after point 72 at around 800 ms. This is achieved as discussed above with the rotary damper 100 arrangement by the damping of the rod 120 controlling movement of the canister 50 via the cam follower teeth 132 of the yoke plate 130. The position of these is illustrated in FIG. 19 for the first time segment 64 below the TBF 60 and for the second time segment 66 above the TBF 62. When the cam follower teeth 132 reach the linear section of the cam track 124 of the rod 120, as discussed above, the rod 120 is able to move axially in the distal direction far more rapidly in this second time segment, as is illustrated in FIG. 19 from point 72 to 74. Again the movement of the rod at this stage of operation is very rapid, allowing the canister 50 to quickly return to the rest position, after the valve 54 has been held open for the first time segment. The valve 54 refills its metering chamber with a subsequent dose during the upstroke (i.e. as the canister 50 moves from position 72 towards 74). There is an ideal range of periods for which the valve 54 is required to be open for refilling; leaving the valve 54 open for a long period (for example to the atmosphere when it is compressed and has delivered a dose) may detrimentally affect the following dose. This Time To Refill, TTR 62, should be, for example, less than 2 seconds in the FIG. 19 embodiment, as indicated by line 82. As is shown in FIG. 19, this embodiment is particularly effective as the canister 50 transitions rapidly to its closed configuration, well in advance of the maximum allowed time before refill may be adversely affected. Indeed this embodiment shown in FIG. 19 operates very closely to the ideal performance illustrated in FIG. 20, in which TBF is substantially equal to TTR and the bypass coincides with the fire point.

Therefore inhalers in accordance with the embodiments of the present invention address at least one of the drawbacks of the prior art, providing automatic resetting of a canister and its valve to improve performance of the inhaler and its reliability and consistency between doses over the full lifetime of the device.

The invention claimed is:

1. An inhaler for delivery of a medicament by inhalation, the inhaler comprising:
   an inhaler body for receiving a canister having a dispensing valve;
   a drive mechanism comprising a biasing member and a displaceable member, the drive mechanism for driving the canister, when received in the inhaler body, from a rest position in which the dispensing valve is closed to at least an actuating position in which the dispensing valve is open, the drive mechanism driving the canister when the biasing member is released from a loaded configuration to move the displaceable member from a first position to a second position;
   a resetting mechanism for resetting the drive mechanism by moving the displaceable member from the second position to the first position and reloading the biasing member to the loaded configuration; and
   a return mechanism for returning the canister from the actuating position to the rest position;
   wherein the return mechanism comprises a damping system including a rotary damper, the damping system configured to enable the canister to automatically return from the actuating position to the rest position within a predetermined time period measured from the release of the biasing member from the loaded configuration, and the rotary damper configured to assist in controlling a speed of the canister during at least a portion of movement of the canister between the actuating position and the rest position.

2. The inhaler of claim 1, wherein the damping system is configured such that the predetermined time period comprises a first time segment and a second time segment, wherein movement of the canister from the actuating position to the rest position is slower during the first time segment than during the second time segment.

3. The inhaler of claim 2, wherein the damping system is configured such that the second time segment immediately follows the first time segment.

4. The inhaler of claim 1, wherein the damping system is configured such that the predetermined time period comprises a first time segment and a second time segment, wherein the canister is maintained in the actuating position during the first time segment and returns from the actuating position to the rest position during the second time segment.

5. An inhaler for delivery of a medicament by inhalation, the inhaler comprising:
   an inhaler body for receiving a canister having a dispensing valve;
   a drive mechanism comprising a biasing member and a displaceable member, the drive mechanism for driving the canister, when received in the inhaler body, from a rest position in which the valve is closed to at least an actuating position in which the valve is open, the drive mechanism driving the canister when the biasing member is released from a loaded configuration to move the displaceable member from a first position to a second position;
   a resetting mechanism for resetting the drive mechanism by moving the displaceable member from the second position to the first position and reloading the biasing member to the loaded configuration; and
   a return mechanism for returning the canister from the actuating position to the rest position;
   wherein the return mechanism comprises a damping system, the damping system configured to enable the canister to automatically return from the actuating position to the rest position within a predetermined time period measured from the release of the biasing member from the loaded configuration, and wherein the damping system comprises a rotary damper that is configured to assist in controlling a speed of the canister during at least a portion of movement of the canister between the actuating position and the rest position.

6. The inhaler of claim 5, wherein the damping system further comprises a rod, the rod coupled with a shaft of the rotary damper such that the rod rotates with the shaft, the rod rotation being controlled by the shaft rotation in at least a first direction of rotation, wherein the rod is moveable relative to the shaft in an axial direction.

7. The inhaler of claim 6, wherein the displaceable member comprises a cam follower and the rod comprises a cam track for receiving the cam follower, the cam track and the cam follower being configured such that the cam follower abuts an edge of the cam track and applies an axial moving force to the rod when the displaceable member moves from the first position to the second position.

8. The inhaler of claim 7, wherein the cam track and the cam follower are configured such that the axial moving force applied by the cam follower to the edge of the cam track axially moves the rod in a direction away from the shaft and the rod thereby applies a driving force to the canister to drive the canister from the rest position to at least the actuating position.

9. The inhaler of claim 7, wherein the cam track comprises at least a first section and a second section, the first section being substantially aligned with the axis of the rod and the second section being curved about a portion of the outer surface of the rod in a direction substantially away from the first section of the track.

10. The inhaler of claim 9, wherein the first section of track is configured to allow axial movement of the rod relative to the cam follower and the second section of the track is configured to allow axial and rotational movement of the rod relative to the cam follower.

11. The inhaler of claim 10, wherein the rotational movement of the rod is damped by the rotational damper and the axial movement of the rod is not damped by the rotational damper.

12. The inhaler of claim 9, wherein the second section of the track is substantially helical about the portion of the outer surface of the rod.

13. The inhaler of any one of claim 7, wherein the rod comprises a pair of cam tracks diametrically opposed on the rod outer surface.

14. The inhaler of any one of claim 7, wherein the cam track is configured such that a first section of the cam track is configured such that the damping system enables the canister to automatically return from the actuating position to the rest position initially at a first speed and is further configured such that the damping system enables the canister to automatically return from the actuating position to the rest position at a second speed at a later time within the predetermined time period.

15. The inhaler of claim 5, further comprising a load-relieving mechanism configured to support at least one of the displaceable member at least a part of the damping system in a spaced apart position in which the displaceable member and/or the part of the damping system is not in contact with the canister, when the canister is received in the inhaler body.

16. A method of dispensing medicament from an inhaler, the method comprising:
- releasing a biasing member of a drive mechanism of the inhaler from a loaded configuration;
- moving, by the released biasing member, a displaceable member of the drive mechanism from a first position to a second position to drive a canister, received in a body of the inhaler, from a rest position, in which a valve of the canister is closed, to at least an actuating position, in which the valve is open;
- automatically returning the canister from the actuating position to the rest position within a predetermined time period measured from the release of the biasing member from the loaded configuration, the automatic return of the canister being regulated by a return mechanism comprising a damping system having a rotary damper configured to assist in controlling a speed of a canister during at least a portion of movement of the canister between the actuating position and the rest position; and
- resetting the drive mechanism with a resetting mechanism that moves the displaceable member from the second position to the first position and reloads the biasing member to the loaded configuration.

17. The method of claim 16, wherein the step of automatically returning the canister within the predetermined time period comprises automatically returning the canister during a first time segment during which movement of the canister from the actuating position to the rest position is slower than during a second time segment.

18. The method of claim 16, wherein the step of automatically returning the canister within the predetermined time period comprises maintaining the canister in the actuating position during a first time segment and automatically returning the canister from the actuating position to the rest position during a second time segment.

* * * * *